United States Patent [19]

Barner et al.

[11] 4,138,289
[45] Feb. 6, 1979

[54] PROCESS FOR THE MANUFACTURE OF TERTIARY, OPTICALLY ACTIVE ALIPHATIC COMPOUNDS

[75] Inventors: Richard Barner, Witterswil; Walter Boguth, Riehen; Hans G. W. Leuenberger, Arlesheim; Max Schmid, Zurich; Reinhard Zell, Rodersdorf, all of Switzerland

[73] Assignee: Hoffmann-La Roche Inc., Nutley, N.J.

[21] Appl. No.: 793,093

[22] Filed: May 2, 1977

[30] Foreign Application Priority Data

May 10, 1976 [AT] Austria .................................. 3407/76
Feb. 18, 1977 [CH] Switzerland ......................... 2064/77

[51] Int. Cl.$^2$ ............................................. C12D 13/02
[52] U.S. Cl. ..................................... 195/30; 195/51 R
[58] Field of Search ................................ 195/30, 51 R

[56] References Cited

U.S. PATENT DOCUMENTS 3,562,112  2/1971  Gibian et al. .......................... 195/30

OTHER PUBLICATIONS

Wallen et al., Type Reactions in Fermentation Chemistry, ARS-71-13, Agriculture Research Service, Dept. of Agriculture, (May, 1959), pp. 280-287.

Primary Examiner—Thomas G. Wiseman
Attorney, Agent, or Firm—Jon S. Saxe; Bernard S. Leon; William H. Epstein

[57] ABSTRACT

A process for asymmetrically hydrogenating through the use of microorganisms a double bond connected to tertiary carbon atom in an olefinic aliphatic compound to produce a tertiary, optically active aliphatic compound useful as an intermediate for optically active Vitamins E and K.

24 Claims, No Drawings

PROCESS FOR THE MANUFACTURE OF TERTIARY, OPTICALLY ACTIVE ALIPHATIC COMPOUNDS

SUMMARY OF INVENTION

The process in accordance with the invention is characterized in that an aerobic or facultative aerobic microorganism, which hydrogenates a double bond situated in an aliphatic chain between CH and methylated C, is allowed to act on a compound of the general formula $$X-CH=\overset{CH_3}{\underset{|}{C}}-Y \qquad I$$

wherein X is carboxy, esterified carboxy, hydroxymethyl etherified or esterified hydroxymethyl and Y is carboxy, formyl, hydroxymethyl, esterified carboxy, acetalized formyl or etherified or esterified hydroxymethyl; with the proviso that X and Y are different functional groups; with the further proviso that when X is hydroxymethyl or esterified hydroxymethyl, Y is carboxy, formyl, acetalized formyl and with the still further proviso that when Y is hydroxymethyl or esterified hydroxymethyl, X is esterified carboxy or alkyl-etherified hydroxymethyl, in an aqueous medium and the obtained product of the general formula $$X'-CH_2-\overset{CH_3}{\underset{\underset{H}{|}}{\overset{\equiv}{C}}}-Y' \qquad II$$

wherein one of X' and Y' is carboxy, esterified carboxy and the other is carboxy, hydroxymethyl, esterified carboxy or etherified or esterified hydroxymethyl; with the proviso that X' and Y' are differing functional groups and with the further proviso that free carboxy and hydroxymethyl groups are lactonized with one another with the formation of the group —CO—O—CH$_2$— or —CH$_2$—O—CO—, and with the still further proviso that where X' is alkyl-etherified hydroxymethyl, Y' can also be hydroxymethyl or esterified hydroxymethyl, is optionally converted into optically active Vitamin E, Vitamin E ester or Vitamin K$_1$.

The process in accordance with the invention offers a novel advantageous route to natural, optically active Vitamin E, Vitamin E ester and Vitamin K$_1$ which hitherto has to be produced from natural products or also by expensive synthetic methods in an uneconomical manner. By the novel process in accordance with the invention there are accordingly obtained, in an especially simple manner, partially novel, optically active compounds of the formula II which can be built up in an advantageous manner to the mentioned optically active vitamins. In toto, therefore, the novel route to natural, optically active Vitamin E, esters thereof and Vitamin K$_1$, including the process in accordance with the invention itself, represents a valuable addition to the state of the art.

DETAILED DESCRIPTION

The above defined stipulation that X and Y have functional significances differing from one another is to be understood so that one of the two residues can react selectively, i.e. with the exclusion of the other residue. Thus, X and Y cannot both simultaneously signify for example carboxy; likewise, they cannot both simultaneously represent esterified carboxy. On the other hand, e.g., one of the substituents X and Y can represent carboxy and the other can represent esterified carboxy, because the carboxy group can be selectively reduced to the hydroxymethyl group (see hereinafter). X and Y cannot both simultaneously represent hydroxymethlyl or etherified or esterified hydroxymethyl, also not combinations of these significances; but X can signify alkyl-etherified hydroxymethyl and Y can signify hydroxymethyl or esterified hydroxymethyl because alkoxymethyl remains inert in the case of saponification, halogenation and magnesium- or phosphorus-organic reactions in contrast to hydroxymethyl or esterified hydroxymethyl.

The carboxy or esterified carboxy groups, hydroxymethyl, etherified or esterified hydroxymethyl groups or acetalized formyl groups quoted under the significance of X and Y are of conventional nature. Esterified carboxyl residues are, for example, residues of the formula R$_1$OOC—, in which R$_1$ represents lower alkyl, phenyl or phenyl-lower alkyl. Esterified/etherified hydroxymethyl residues are, for example, residues of the formula R$_2$OCH$_2$—, in which R$_2$ represents a lower acyl group, e.g., lower alkanoyl, benzoyl or phenyl-lower alkanoyl, or an ether protecting group, e.g., lower alkyl or a group of the formula R$_3$O—CHR$_4$—, in which R$_3$ represents lower alkyl and R$_4$ represents hydrogen or lower alkyl or together with R$_3$ n-butylene (2-tetrahydropyranyl). Acetalized formyl groups are, for example, residues of the formula

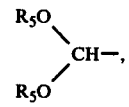

in which R$_5$ signifies lower alkyl or both substituents R$_5$ together represent lower alkylene. In the residues X and Y any present lower alkyl, lower alkoxy, lower alkylene and lower alkanoyl groups, alone or in combinations [such as phenyl-lower alkyl, phenyl-lower alkanoyl, di-(lower-alkoxy)-methyl], represent straight-chain or branched groups which preferably carry up to 4 carbon atoms. Examples are methyl, ethyl, n-propyl, isopropyl, n-butyl, isobutyl, sec-butyl, t-butyl; methoxy, ethoxy, n-propoxy, isopropoxy, n-butoxy, isobutoxy, sec-butoxy, t-butoxy; methylene, ethylene, n-propylene, 1-methyl-ethylene, 1,2-dimethyl-ethylene; acetyl, propionyl, n-butryl, isobutyryl.

X and Y in the significance carboxy or formyl are preferably esterified or acetalized. Preferred groups R$_1$ in esterified carboxy groups R$_1$OOC— are methyl and ethyl; preferred groups R$_5$ in acetalized formyl groups

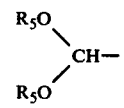

are methyl and ethyl as well as (both R$_5$ together) ethylene and 1,3-propylene.

X and Y in the significance hydroxymethyl can be unsubstituted or etherified or esterified. Where the hydroxymethyl group is substituted, the substituent preferably represents methyl, acetyl or benzoyl.

In carrying out the conversion of a compound of formula I to a compound of formula II, any aerobic or facultative microorganism capable of hydrogenating a double bond situated in an aliphatic chain between a CH and methylated CH moiety can be utilized.

The microorganism used in accordance with the invention possesses aerobic or facultative aerobic character, i.e. it has the capability to grow not only under aerobic but also under anaerobic conditions (facultative aerobic microorganism) or also only under aerobic conditions (aerobic microorganism). By testing out any aerobic or facultative aerobic yeasts, fungi or bacteria on the educt of the formula I employed in accordance with the invention it is easy to find a suitable microorganism which is in a position to hydrogenate the double bond situated between CH and methylated C and which can thereby be employed in the process in accordance with the invention. Preferred usable known microorganisms are:

| | | |
|---|---|---|
| 1) | | Eucaryontes |
| | 1.1. | Yeasts of the genera |
| | | Candida |
| | | e.g. C. albicans |
| | | C. guillermondii |
| | | Kloechera |
| | | e.g. K. brevis |
| | | Rhodotorula |
| | | e.g. R. rotundata |
| | | Saccharomyces |
| | | e.g. S. carlsbergensis |
| | | S. cerevisiae |
| | | S. cer. elliposides |
| | | Torulopsis |
| | | e.g. T. apicola |
| | | T. rotundata |
| | 1.2. | Fungi of the genera |
| | | Absidia |
| | | e.g. A. regneri |
| | | Aspergillus |
| | | e.g. A. clavatus |
| | | A. fumigatus |
| | | A. ochraceus |
| | | A. niger |
| | | Colletotrichum |
| | | e.g. C. gloeosporoides |
| | | Cunninghamella |
| | | e.g. C. blakesleeana |
| | | Curvularia |
| | | e.g. C. lunata |
| | | Geotrichum |
| | | e.g. G. candidum |
| | | Gibberella |
| | | e.g. G. fujikuroi |
| | | Gliocladium |
| | | e.g. G. roseum |
| | | Mucor |
| | | e.g. M. circinelloides |
| | | M. corymbifer |
| | | M. griseo-cyanus |
| | | M. hiemalis |
| | | M. parasiticus |
| | | M. spinosus |
| | | Penicillium |
| | | e.g. P. notatum |
| | | P. novae-zeelandiae |
| | | P. viride |
| | | Phycomyces |
| | | e.g. P. blakesleeanus |
| | | Rhizopus |
| | | e.g. R. arrhizus |
| | | R. circinans |
| | | Trichothecium |
| | | e.g. T. roseum |
| 2. | | Procaryontes |
| | 2.1. | Mycelia-forming bacteria (Actinomycetes) of the genera |
| | | Mycobacterium |
| | | e.g. M. butyricum |
| | | M. rhodochrous |
| | | Streptomyces |
| | | e.g. S. fradiae |
| | | S. rimosus |
| | | Proactinomyces |
| | | e.g. P. restrictus |
| | | P. roseus |
| | 2.2. | Gram-positive bacteria of the genera |
| | | Bacillus |
| | | e.g. B. subtilis |
| | | Micrococcus |
| | | e.g. M. lysodeikticus |
| | | Propionibacterium |
| | | e.g. P. shermanii |
| | | Pediococcus |
| | | e.g. P. cerevisiae |
| | | Streptococcus |
| | | e.g. S. faecalis |
| | | A. lactis |
| | 2.3. | Gram-negative bacteria of the genera |
| | | Azotobacter |
| | | e.g. A. indicus |
| | | Pseudomonas |
| | | e.g. P. fluorescens |
| | | Serratia |
| | | e.g. S. marcescens |
| | | Vibrio |
| | | e.g. V metschnikovii |

Preferred microorganisms in the process in accordance with the invention are, as evident from the procedures hereinafter, Saccharomyces cerevisiae (pressed yeast; bakers yeast) and Geotrichum candidum. S. cerevisiae is obtainable on the market as commercial pressed yeast. Also, G. candidum is a known microorganism which is generally accessible from recognized depositories. In order to safeguard the practicability of the process with the use of G. candicum a culture of the strain used was, however, deposited at the Centraalbureau voor Schimmelcultures in Baarn, Holland, under the number CBS 233.76.

It is evident that each of the microorganisms employed in accordance with the invention should be cultivated prior to the use in the fermentation in accordance with the invention; the cultivation is generally effected in a manner known per se in an aqueous medium with the aid of the usual nutrient materials, i.e., in the presence of a carbon source, such as glucose, fructose, saccharose and/or maltose, a nitrogen source, such as urea, peptone, yeast extract, meat extract, amino acids and/or ammonium salts, in organic salts, such as magnesium (sic), sodium postassium, calcium and/or ferrous salts, other growth-promoting substances, such as vitamins and the like. It is often conventient to use the cultivation medium likewise in the fermentation in accordance with the invention, although — as more precisely illustrated hereinafter the composition of the fermentation medium used in accordance with the invention can be substantially simpler.

The fermentation in accordance with the invention is feasible without further additiives than the educt of the formula I and the microorganism to be used. It is however, advantageous to add to the aqueous medium an assimilable carbon source as the microorganism nutrient material, preferably in an amount of from about 10 to about 100 g per liter, for example in the form of a sugar, such as glucose, fructose, saccharose, maltose and the like, in order that the viability of the microorganism and the metabolic activity associated therewith remains as long as possible. More than 100 g of carbon source per liter of nutrient medium do not influence the results, but bring no advantage over the case where the amount of from 10 to about 100 g carbon source are employed. The addition of a nitrogen source is not necessary; if desired, there can, however, be added an asimmilable nitrogen source, preferably in an amount of from about 1 to about 50 g per liter, for example, in the form of urea, peptone, yeast extract, meat extract, amino acids, ammonium salts and the like. The culture medium can further also contain inorganic salts, such as magnesium, sodium, potassium, calcium and/or ferrous salts, other growth-promoting substances, such as vitamins and the like.

The pH-value of the fermentation should preferably lie within the range of 2 to 10, especially 3 to 8 and is for the most part attainable without particular additives. If desired, the pH-value can be regulated by the use of buffers, e.g., phosphate, phthalate or tris buffer [tris-(hydroxymethyl)-aminomethane]. The temperature can vary in a wide range, e.g. of from about 10° to 40° C., a temperature of 20–35° C. being preferred. For the purpose of obtaining optimal yields it is preferred that the educt of the formula I is present in the fermentation broth in a concentration of from about 0.1 to about 5.0%, especially from about 1.0 to about 2.5% of the broth.

After reaction has occurred, more educt can be added, in a preferred concentration between 0.2 and 1.5%. This process can be repeated until inactivation of the microorganism. The substrate can also be added continuously with the help of a pump.

The useful fermentation time is dependent on the microorganism used, but varies in the case of singel educt addition for the most part from about 4 to about 250 hours, especially from about 1 to about 2 days.

The fermentation is preferably carried out aerobically, e.g., while stirring, shaking or by means of an air throughput. For the control of foam there can be added the customary anti-foam agents, such as silicon oils, polyalkyleneglycol derivatives, soya bean oil and the like. There is preferably used a microorganism which is in the non-growing (stationary) phase. By choice of a stationary microorganism the advantage is achieved that the fermentation procedure need not be carried out under sterile conditions if there is used a nutrient medium which permits no substantial reproduction of microorganisms, for example a nutrient medium without nitrogen source.

Depending on the choice of the educt of the formula I and of the microorganism, this is subjected to different transformations or there are obtained different products of the formula II. The process in accordance with the invention can be classified according to these aspects into five sub-groups A, B, C, D and E:

(A) With the use of educts of the general formula

wherein $X_A$ is carboxy or esterified carboxy and $Y_A$ is formyl or acetalized formyl or $X_A$ is esterified carboxy and $Y_A$ is hydroxymethyl, etherified or esterified hydroxymethyl, there are obtained with the choice of suitable microorganisms fermentation products of the formula II, in which X' is carboxy or esterified carboxy and Y' is hydroxymethyl or etherified or esterified hydroxymethyl, free carboxy and hydroxymethyl groups being lactonized with one another with the formation of the group —CO—O—CH$_2$—. The lactonized product is the (S)-dihydro-4-methyl-2-(3H)-furanone of the formula

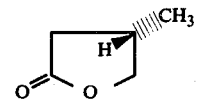

The fermentation brings about the saturation of the double bond with the formation of an optically uniform compound as well as also the reduction of the formyl group of hydrolysis and reduction of the acetalized formyl group into hydroxymethyl. Possible substituents on carboxy or hydroxymethyl are less readily hydrolyzable, and these groups can remain partially intact in the first instance after the saturation of the double bond. Corresponding fermentation products of the formula II, which are still substituted on carboxy and/or hydroxymethyl, can be isolated as such from the fermentation broth, or they can be converted by lengthening the fermentation duration, e.g., up to 3 to 10 days, into the lactone of the formula IIa by splitting off the substituents on carboxy or hydroxymethyl; the fermentation product thereby undergoing a lactone ring closure with the formation of the lactone of the formula IIA defined above. The lactone ring closure can further also occur with the purification of a fermentation product of the formula II, in which X' represents esterified carboxy and Y' represents hydroxymethyl (e.g., by distillation, preferably under slightly acidic, e.g., p-toluene acidic, conditions). The cleavage of the substituents on carboxy or hydroxymethyl can likewise be effected by alkaline saponification.

Where, in formula IA, $Y_A$ represents an alkyl-etherified, e.g., methyl-etherified, hydroxymethyl group, this alkyl group remains intact after the fermentation. There are obtained fermentation products of the formula II, in which X' represents carboxy or esterified carboxy and Y' represents alkoxymethyl.

For the fermentation of the educt of the formula IA Saccharomyces cerevisiae (pressed yeast, bakers yeast) is preferably used as the microorganism. According to a preferred embodiment there is used a starting compound of the formula IA, in which $X_A$ represents carboxy or esterified carboxy and $Y_A$ is formyl or optionally acetalized formyl. For this embodiment there can be used, for example, the following microorganisms:

| 1. | Eucaryontes | |
|---|---|---|
| | 1.1 | Yeasts of the genera |
| | | *Candida* |
| | | e.g. *C. utilis* |
| | | *Kloeckera* |
| | | e.g. *K. brevis* |
| | | *Saccharomyces* |
| | | e.g. *S. carlsbergensis* |
| | |     *S. cerevisiae* |
| | |     *S. cer. ellipsoides* |
| | | *Torulopsis* |
| | | e.g. *T. apicola* |
| | 1.2. | Fungi of the genera |
| | | *Absidia* |
| | | e.g. *A regneri* |
| | | *Aspergillus* |
| | | e.g. *A. niger* |
| | | *Colletotrichum* |
| | | e.g. *C. gloeosporioides* |
| | | *Cunninghamella* |
| | | e.g. *C. blakesleeana* |
| | | *Gibberella* |
| | | e.g. *G. fujikuroi* |
| | | *Gliocladium* |
| | | e.g. *G. roseum* |
| | | *Mucor* |
| | | e.g. *M. circinelloides* |
| | |     *M. griseo-cyanus* |
| | |     *M. parasiticus* |

| | | |
|---|---|---|
| | | *Penicillium* |
| | | e.g. *P. novae-zeelandiae* |
| | | *Phycomyces* |
| | | e.g. *P. blakesleeanus* |
| | | *Rhizopus* |
| | | e.g. *R. arrhizus* |
| | | *R. circinans* |
| | | *Trichothecium* |
| | | e.g. *T. roseum* |
| 2. | Procaryontes | |
| | 2.1. | Mycelia-forming bacteria (Actinomycetes) of the genera |
| | | *Mycobacterium* |
| | | e.g. *M. butyricum* |
| | 2.3. | gram-negative bacteria of the genera |
| | | *Azotobacter* |
| | | e.g. *A. indicus* |

In accordance with an especially preferred process there is used as the starting compound of the formula I ethyl-trans-4,4-dimethyoxy-3-methylcrotonate and as the microorganism Saccharomyces cerevisiae, there being obtained as the fermentation product of the formula II chiefly (S)-3-methyl-4-hydroxy-butyric acid ethyl ester. Acid hydrolysis of this compound in the manner described above yields the (S)-dihydro-4-methyl-2(3H)-furanone.

(B) With the use of educts of the general formula

IB wherein one of $X_B$ and $Y_B$ is carboxy and the other is esterified carboxy, there are obtained with the choice of suitable microorganisms fermentation products of the formula II, wherein one of the residues X' and Y' represents carboxy and the other represents esterified carboxy. There is accordingly brought about only the stereospecific saturation of the double bond. Saccharomyces cerevisiae is preferably used as the microorganism for this reaction. There is especially used as the starting compound of the formula IB one such wherein $X_B$ represents esterified carboxy and $Y_B$ represents carboxy.

(C) With the use of educts of the general formula

IC wherein $X_C$ is esterified carboxy and $Y_C$ is formyl, hydroxymethyl, acetalized formyl or esterified hydroxymethyl, there can be brought about with the use of suitable microorganisms in addition to the stereospecific saturation of the double bond an oxidation or hydrolysis and oxidation of the formyl or acetalized formyl group or of the hydroxymethyl or of the esterified hydroxymethyl group, and there are obtained fermentation products of the formula II, wherein X' represents esterified carboxy and Y' represents carboxy. This reaction is preferably brought about by the fungus Geotrichum candidum.

(D) With the use of educts of the general formula

ID wherein $X_D$ is hydroxymethyl or esterified hydroxymethyl and $Y_D$ is formyl, acetalized formyl or esterified carboxy, there are obtained with the choice of suitable microorganisms fermentation products of the formula II, wherein X' is hydroxymethyl and Y' is esterified carboxy, free carboxy and hydroxymethyl groups being lactonized with one another with the formation of the group —CH₂—O—CO—. The lactonized product is the (S)-dihydro-3-methyl-2(3H)-furanone of the formula

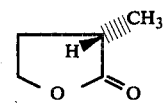

IID

Accordingly, there is brought about on the one hand a stereospecific saturation of the double bond, on the other hand optionally acetalized formyl groups present are subjected to an oxidation or a hydrolysis and oxidation.

The optionally present acetal or ester substituents on hydroxymethyl or the optically present ester substituents on the carboxy are, as also in the case of the subgroup A) above, less readily hydrolysable than the substituents on formyl and can remain partially intact in the first instance after the saturation of the double bond. They can be split off by lengthening the fermentation, the lactone of the formula IID being obtained.

The fungus Geotrichum candidum is preferably used as the microorganism for this embodiment of the process in accordance with the invention. According to a preferred embodiment there is used a starting compound of the formula ID, in which $X_D$ is hydroxymethyl or esterified hydroxymethyl (Preferably free hydroxymethyl) and $Y_E$ is formyl or acetalized formyl (preferably acetalized formyl). For this embodiment there can be used, for example, the following microorganisms:

| | | |
|---|---|---|
| 1. | Eucaryontes | |
| | 1.1. | Yeasts of the genera |
| | | *Candida* |
| | | e.g. *C. albicans* |
| | | *C. guillermondii* |
| | | *Rhodotorula* |
| | | e.g. *R. rotundata* |
| | | *Saccharomyces* |
| | | e.g. *S. cerevisiae* |
| | | *Torylopsis* |
| | | e.g. *T. apicola* |
| | | *T. rotundata* |
| | 1.2. | Fungi of the genera |
| | | *Aspergillus* |
| | | e.g. *A. clavatus* |
| | | *A. fischeri* |
| | | *A. flavus* |
| | | *A. fumigatus* |
| | | *A. ochraceus* |
| | | *A. niger* |
| | | *Curvularia* |
| | | e.g. *C. lunata* |
| | | *Cylindrocarpon* |
| | | e.g. *C. radicicola* |
| | | *Mucor* |
| | | e.g. *M. corymbifer* |
| | | *M. griseo-cyanus* |
| | | *M. hiemalis* |
| | | *M. parasiticus* |
| | | *M. spinosus* |
| | | *Penicillium* |
| | | e.g. *P. notatum* |
| | | *P. viride* |
| | | *Rhizopus* |
| | | e.g. *R. arrhizus* |
| | | *R. circinans* |
| | | *Absidia* |
| | | e.g. *A. regneri* |
| | | *Geotrichum* |
| | | e.g. *G. candidum* |

| | | -continued |
|---|---|---|
| | | *Gibberella* |
| | | e.g. *Gibberella fujikuroi* |
| | | *Gliocladium* |
| | | e.g. *G. roseum* |
| | | *Phycomyces* |
| | | e.g. *P. blakesleeanus* |
| 2. | | Procaryontes |
| | 2.1. | Mycelia-forming bacteria (Actinomycetes) of the genera |
| | | *Mycobacterium* |
| | | e.g. *M. butyricum* |
| | | *M. rhodochrous* |
| | | *Streptomyces* |
| | | e.g. *S. fradiae* |
| | | *S. rimosus* |
| | | *Proactinomyces* |
| | | e.g. *P. restrictus* |
| | | *P. roseus* |
| | 2.2. | Gram-positive bacteria of the genera |
| | | *Bacillus* |
| | | e.g. *B. subtilis* |
| | | *Micrococcus* |
| | | e.g. *M. lysodeikticus* |
| | | *Propionibacterium* |
| | | e.g. *P. shermanii* |
| | | *Pediococcus* |
| | | e.g. *P. cerevisiae* |
| | | *Streptococcus* |
| | | e.g. *S. faecalis* |
| | | *S. lactis* |
| | 2.3. | Gram-negative bacteria of the genera |
| | | *Pseudomonas* |
| | | e.g. *P. fluorencens* |
| | | *Serratia* |
| | | e.g. *S. marcescens* |
| | | *Vibrio* |
| | | e.g. *V. metschnikovii* |

In accordance with an especially preferred process there is used as the starting compound of the formula I trans-3-(1,3-dioxolan-2-yl)-2-buten-1-ol and as the microorganism Geotrichum candidum, there being obtained as the fermentation product the (S)-dihydro-3-methyl-2(3H)-furanone of the formula IID.

Where, in formula ID, $X_D$ is hydroxymethyl or esterified hydroxymethyl and $Y_D$ is esterified carboxy, Geotrichum candidum likewise yields the end product given above, but higher yields are obtained by use of Saccharomyces cerevisiae.

(E) With the use of educts of the general formula

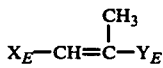
$$X_E-CH=C(CH_3)-Y_E \qquad \text{IE}$$

wherein $X_E$ is alkyl-etherified hydroxymethyl and $Y_E$ is formyl or acetalized formyl or hydroxymethyl or esterified hydroxymethyl, there are obtained with the choice of suitable microorganisms fermentation products of the formula II, wherein X' represents alkyl-etherified hydroxymethyl and Y' represents carboxy or optionally esterified hydroxymethyl. It is characteristic for this educt group that the alkoxymethyl group $X_E$ remains unaltered during the fermentation.

With Saccharomyces cerevisiae there is realized, for example, a reduction or hydrolysis and reduction of the formyl or acetalized formyl group $Y_E$ into hydroxymethyl, while esterified hydroxymethyl groups $Y_E$ remain unaltered. With Geotrichum candidum there is brought about an oxidation or hydrolysis and oxidation of the formyl or acetalized formyl group as well as also of the hydroxymethyl or esterified hydroxymethyl group $Y_E$ into carboxy.

After completion of the cultivation, the fermentation product is isolated from the fermentation broth in the customary manner. There preferably comes into consideration extraction with a non-water soluble organic solvent, for example, with chlorinated or non-chlorinated, aliphatic or cycloaliphatic, hydrocarbon, such as n-hexane, cyclohexane, methylene chloride, chloroform, carbon tetrachloride, an aliphatic ester, such as ethyl acetate, n-butyl acetate, amyl acetate or an aliphatic ether, such as dimethyl ether or diisopropyl ether. Methylene chloride is a preferred solvent. For the avoidance of emulsions there can be used extraction in the continuous process, or extraction by multiplicative distribution. According to a preferred isolation method, the fermented broth is filtered or centrifuged and the aqueous phase and the sediment worked-up separately. The curde product obtained can be purified in the customary manner., e.g., by fractional distillation. As already mentioned, open intermediate products of the formula II obtained (with the exception of the alkyl ether) can be converted into the corresponding lactone of the formula IIA or IID during the workingup.

The product of the formula II obtained can be converted into optically active vitamin E or $K_1$, for example, as follows:

Ester groups on hydroxymethyl or on carboxy can be split off hydrolytically, preferably by basic hydrolysis. The corresponding lactone is obtained. In order to obtain optically pure lactone there are preferably employed for the hydrolysis such esters which lead to the lactone of the formula IIA.

Fermentation products of the formula II, in which one of the residues X' and Y' represents carboxy and the other represents esterified carboxy, (sub-group B above) can be selectively reduced chemically, the free carboxy group being transformed into hydroxymethyl. This reduction is effected, e.g., by treatment with a boron hydride/dimethylsulfide complex, preferably in an ethereal solvent, such as tetrahydrofuran, and at a temperature of about −10° C. to room temperature. The carboxy protecting group can be split off in a manner known per se, the lactone of the formula IIA or IID being obtained. The selective reduction is preferably carried out on a fermentation product of the formula II, wherein X' represents esterified carboxy and Y' represents carboxy; the lactone of the formula IIA being thereby obtained.

The lactones of the formulae IIA and IID can be converted into natural, optically active vitamin E, vitamin E ester and vitamin $K_1$ in accordance with the following reaction scheme:

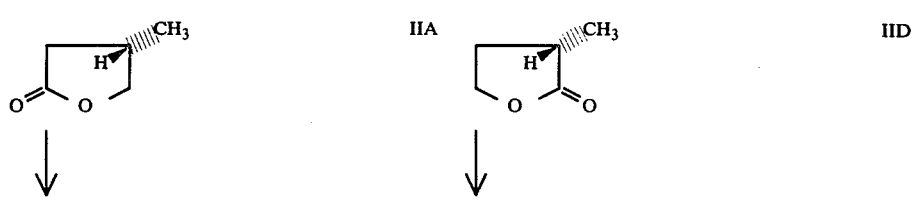

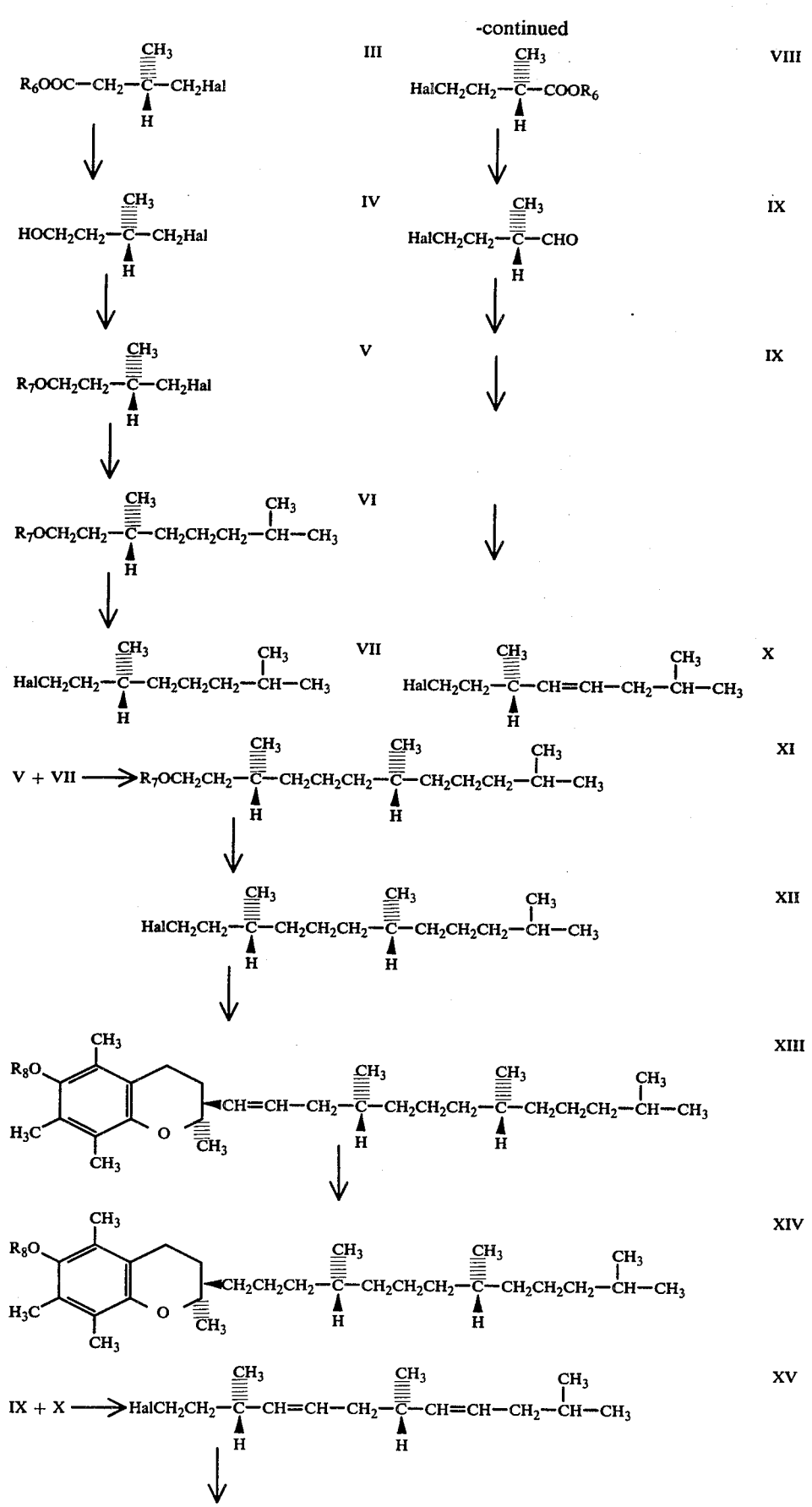

-continued

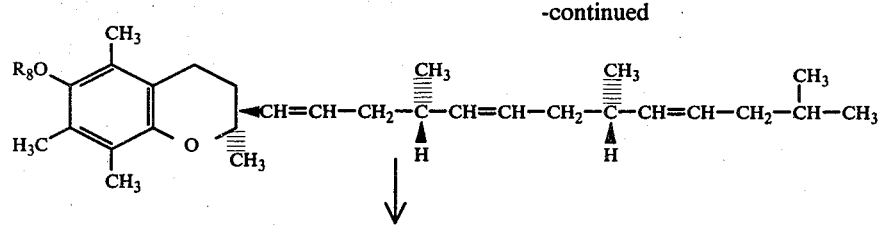 XVI

↓

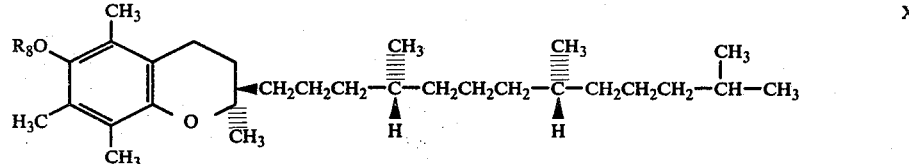 XIV

XV ⟶ XII ⟶ 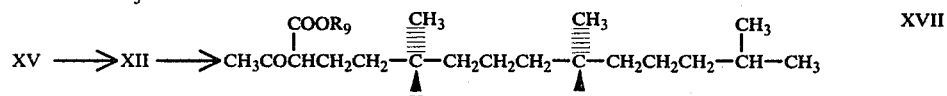 XVII

↓

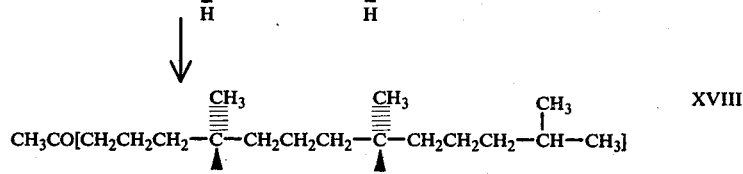 XVIII

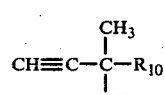

 XIX    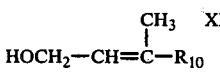 XXI

↓ XX     ↓

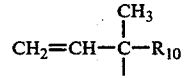   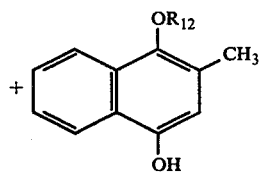 XXIII    XXII

↓

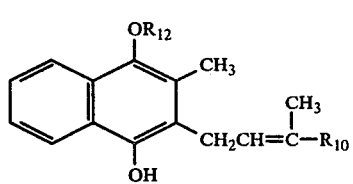 XXIV

↓

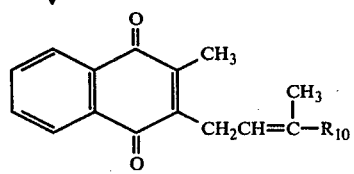 XXV

In the above reaction scheme $R_6$ signifies a carboxyl protecting group, preferably lower alkyl, e.g., methyl or ethyl, $R_7$ signifies a carbonyl-free protecting group cleavable by acid hydrolysis, preferably 2-tetrahydropyranyl, $R_8$ signifies hydrogen or lower alkanoyl, e.g., acetyl, $R_9$ signifies lower alkyl, e.g., methyl or ethyl, $R_{10}$ signifies the group

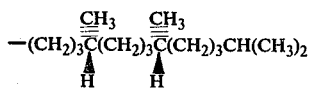

$R_{11}$ signifies lower alkyl, e.g., methyl or ethyl, $R_{12}$ signifies hydrogen or lower acyl, e.g., acetyl or benzoyl, and Hal signifies a halogen atom, e.g., chlorine, bromine or iodine.

The reactions IIA→III and IID→VIII are effected by treatment with hydrogen halide, preferably hydrogen chloride or hydrogen bromide, in an approptiate alcohol for the introduction of the protecting group $R_6$, e.g., in a lower alkanol, such as methanol or ethanol. In place of the lactones IIA and IID there can also be used the corresponding, open fermentation products of the formula II, wherein one of the substituents X' and Y' represents esterified carboxy and the other represents hydroxymethyl.

The ester group of compounds III is reductively transformed into hydroxymethyl with the formation of compounds IV. The reduction is effected, e.g., at $-20°$ to $0°$ C. in an inert organic solvent with an aluminium-organic compound, e.g., a β-branched aluminium-di-lower-alkyl hydride, e.g., diisobutylaluminium hydride or also with lithiumaluminium hydride.

By mild reduction of the ester group in compounds VIII this is transformed into the aldehyde group with the formation of compounds IX, for example, by treatment with a β-branched aluminium-di-lower-alkyl hydride, such as di-isobutylaluminium hydride at $-80°$ to $-40°$ C.

The hydroxy group of compounds IV is protected with an acid-hydrolytically cleavable protecting group $R_7$ with the formation of compounds V. The introduction of this protecting group is effected, e.g., by treatment with the corresponding olefinic compound, such as 3,4-dihydro-2,4-pyran, methyl vinyl ether or 2-methyl-propene.

The chain-lengthening of the $C_5$-compound of the formula V obtained can be carried out by reaction with a 1-halogeno-3-methyl-butane, preferably 1-bromo-3-methylbutane, or with a corresponding sulphonate, preferably 3-methyl-1-butanol-p-toluenesulphonate, with the aid of a magnesium-organic reaction. A bromide of the formula V is preferably used. For the carrying out of the magnesium-organic reaction the compound of the formula V is reacted with metallic magnesium in an ethereal solvent, e.g., tetrahydrofuran, preferably at a temperature between about room temperature and $80°$ C., magnesium being attached. After addition of the second coupling component, as well as a catalytic amount of a di-(alkali metal)-tetrahalogenocuprate, preferably di-lithium-tetrachlorocuprate, there is obtained the desired $C_{10}$-compound of the formula VI. The mentioned ethereal solvent is used as the solvent; the temperature lies in general between about $-80°$ C. and the room temperature. The reaction is preferably started at lower temperature ($-80°$ to $0°$ C.) and subsequently completed at higher temperature, e.g. room temperature.

The group $R_7O-$ in the product of the formula VI obtained is now exchanged for halogen, especially for bromine, chlorine or iodine. This is preferably effected by acid hydrolysis, e.g. with aqueous mineral acid, such as hydrochloric acid, phosphoric acid or sulphuric acid at room temperature, followed by halogenation with the corresponding hydrogen halide or also by treatment with N-chloro- or N-bromosuccinimide and triphenylphosphine, with phosphorus tribromide or chloride or phosphorus pentabromide or chloride, with triphenylphosphorus dibromide or chloride or with methyltriphenoxyphosphonium iodide. A bromo derivative of the formula VII obtained can be transformed into the corresponding iodo derivative by treatment with an alkali metal iodide in a ketonic solvent, e.g., methyl ethyl ketone or methyl isobutyl ketone, at elevated temperature.

For the further chain-lengthening, the compounds V and VII are now reacted with one another, namely with the aid of a magnesium-organic reaction, in substantially the same manner as described above for the chain-lengthening V→VI. There is thus obtained an optically active $C_{15}$-compound of the formula XI which is converted into the halogenide XII in the same manner as for the conversion V→VI just described.

The chain-lengthening of the aldehyde IX is effected with the aid of a phosphorus-organic reaction by reaction with a 3-methylbutyl-triarylphosphonium halogenide, preferably 3-methylbutyl-triphenylphosphonium bromide. The reaction is effected in the presence of a base, such as a lower alkyl lithium, e.g., n-butyllithium, phenyllithium, or an alkali metal hydride or amide, if desired in an inert organic solvent, e.g., in a lower alkane, such as n-hexane, in a chlorinated hydrocarbon, such as methylene chloride, in an ether, such as diethyl ether, in an aprotic, polar solvent, such as dimethyl sulphoxide, dimethylformamide or hexamethylphosphoric acid triamide or in mixtures of these solvents, at a temperature between about $-10°$ C. and room temperature.

For the further chain-lengthening the compounds IX and X are reacted with one another, namely with the aid of a phosphorus-organic reaction, in substantially the same manner as just given for the chain-lengthening IX→X. The optically active halogenide XV is obtained.

The halogenides XII and XV obtained can be converted into natural, optically active vitamin E or 6-ester there (formula XIV) with the aid of the described phosphorus-organic reaction and the (S)-6-hydroxy-2-formyl-2,5,7,8-tetramethyl-2-chromane or the corresponding 6-ester. There are obtained in the first instance the corresponding, unsaturated compounds XIII and XVI with 1 or 3 double bonds in the side chain. These double bonds can be saturated by catalytic hydrogenation. As the catalyst there is preferably used a noble metal catalyst, such as, e.g., one of the platinum dioxide, palladium-carbon, Raney-nickel or Raney-cobalt catalysts customarily used for hydrogenations. The hydrogenation is preferably effected in a lower alkanecarboxylic acid ester, such as ethyl acetate, or in a lower alkanol, such as methanol or ethanol. It is especially worked under normal pressure and at a temperature between the room temperature and about $80°$ C. A possibly obtained product with a free hydroxy group in the 6-position of the chromane portion can be esterified if desired, e.g., with acetic anhydride in pyridine.

The lactones IIA and IID can likewise be used for the manufacture of natural, optically active vitamin $K_1$. Starting from the halogenides XV and XII obtained in the above manner one can proceed as follows:

The halogenides XV are transformed into the halogenides XLL by hydrogenation as in the case of the reactions XIII→XIV and XVI→XIV. A halogenide XII is transformed by the action of an acetic acid lower alkyl ester, e.g., the methyl or ethyl ester, into the ester XVII which undergoes a hydrolysis and decarboxylation with aqueous alkali with the formation of the compound XVIII (hexahydrofarnesylacetone).

The optically active hexahydrofarnesylacetone XVIII is transformed into optically active isophytol XIX according to one variant by reaction with an alkali metal acetylide followed by partial hydrogenation with Lindlar catalyst. By choice, the hexahydrofarnesylacetone XVIII is reacted with a compound of the formula

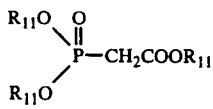

in a lower-alkanolic solvent with the corresponding lower alkali metal alkoxide, e.g., triethylphosphonoacetate in ethanolic sodium ethoxide, to the compound XXI which is converted into optically active phytol XXII by reduction with a complex metal hydride, such as lithium aluminium hydride or diisobutylaluminium hydride.

The isophytol XX or the phytol XXII can be condensed with menadiol or 1-acyl derivative thereof (compound XXIII) with the aid of a Lewis acid, e.g., boron trifluoride, in an ethereal solvent, e.g., dibutyl ether. After saponification of the 1-acyl derivative XXIV obtained, e.g., with methanolic alkali, the optically active vitamin $K_1$ of the formula XXV is obtained by oxidation with air. The portion of the desired trans-product can be increased by separation of the cis- and trans-forms XXI and/or XXIV, for example, by chromatography or recrystallisation.

The conversion of optically active hexahydrofarnesylacetone into natural phytol and natural vitamin $K_1$ is also described in J. Chem. Soc. (C), 1966, pages 2144–2176 (especially 2146, 2151 and 2152) or in Helv. Chim, Acta, 48, 1965, pages 1332–1347 (especially 1333 and 1346).

Fermentation products of the formula

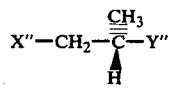

wherein X" is alkyl-etherified hydroxymethyl, e.g., methoxymethyl, and Y" is carboxy, esterified carboxy, hydroxymethyl or esterified hydroxymethyl, can be converted into the corresponding compounds of the formula II", wherein Y" represents hydroxymethyl, the carboxy or esterified carboxy group being reduced in analogy to the above reaction III→IV and the esterified hydroxy group being saponified basically. The alcohol of the formula II" can be transformed with tosyl chloride into the corresponding tosylate. This can be converted with a 1-halogeno-3-methyl-butane, e.g., 1-bromo-3-methyl-butane and metallic magnesium with the aid of di-lithium-tetrachlorocuprate under reaction conditions as are described for the reaction V→VI into the corresponding $C_{10}$-compound, whereafter the alkoxy group is exchanged for halogen with the formation of the above compound VII. Alkoxy is transformed by treatment with boron tribromide or chloride in methylene chloride at about −20° to 0° C. into the hydroxy group which is subsequently halogenated as described above. The conversion of the compound VII into vitamin E, esters thereof of vitamin $K_1$ is effected in the above manner.

In the Examples hereinafter the following depositories are specified:

ATCC = American Type Culture Collection, Rockville, Maryland, USA
CBS = Centraalbureau voor Schimmelcultures, Baarn - Holland
NRRL = Northern Utilization Research and Development Division of U.S.D.A., Peoria, Illinois, USA
NCIB = National Collection of Industrial Bacteria, Aberdeen - Scotland
ETH = Eidgenössische Technische Hochschule, Zürich - Switzerland
PRL = Prairie Regional Laboratories, Sascatoon, Canada All temperatures are given in degrees Centigrade. In the Examples, Torr is mmHg.

EXAMPLE 1

Transformation of trans-3-(1,3-dioxolan-2-yl)-2-buten-1-ol to the (S)-dihydro-3-methyl-2(3H)-furanone by Geotrichum candidum

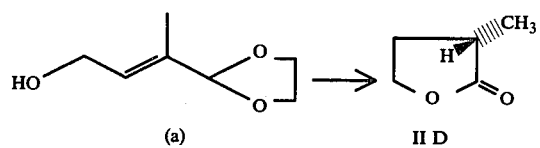

CULTIVATION OF THE MICROORGANISM

The cultivation of the microorganism is effected in a medium of the following composition:

| | | |
|---|---|---|
| 20 | g D(+)-glucose (monohydrate) | in one liter of deionised water (pH 6) |
| 10 | g Yeast extract (Difco) | |
| 16 | g $KH_2PO_4$ | |
| 2.6 | $Na_2HPO_4$ | |

This medium is sterilised at 135° in the autoclave during 30 minutes. The microorganism is inoculated from an agar slant culture into 500 ml of cultivation medium with the use of the customary microbiological working procedures and incubated at 30° in a sterile Erlenmeyer flask with sterile stopper during 48 h on a rotary shaking machine. This batch is then transferred into a sterile laboratory fermenter which contains 20 l of nutrient medium of the composition named above. 10 ml of polypropyleneglycol monobutyl ether are added for the control of foam. The fermenter is operated during 24 h at a thermostatically regulated temperature of 30°, a stirring frequency of 900 r/min and an air-flow rate of 600 l/h. The biomass is subsequently filtered off. 1 kg of biomass is produced from such a 20 l batch. The biomass is stored in the refrigerator until used in the transformation experiment.

Transformation of trans-3-(1,3-dioxolan-2-yl)-2-buten-1-ol (a)

18 l of deionised water and 200 g of saccharose are placed in a clean, but not sterilised, laboratory fermenter (total volume 31 l). 2 kg of biomass (Geotrichum candidum CBS 233.76) are suspended in this sugar solution and 350 g of substrate (a) are subsequently added. This batch is mixed during 24 h at a thermostatically regulated temperature of 30° with a stirrer rotation number of 900 r/min and aerated with an air-flow rate of 600 l/h. After 2,4,6,8 and 24 h, samples of 10 ml each are removed, extracted twice with methylene chloride, dried over $Na_2SO_4$ and concentrated under reduced pressure. The residue is taken up in dioxan and analysed gas-chromatographically (glass column with 12% carbowax as the adsorbent, starting temperature 100° C., temperature increase 4°/min, end temperature 220° C., carrier gas: N₂). The percentage transformation to the optically active fermentation product (S)-dihydro-3-methyl-2(3H)-furanone (IID) is reproduced in Table 1.

Table 1

| Fermentation time | Transformation to the lactone IID |
|---|---|
| 2 h | 11.6% |
| 4 h | 23.9% |
| 6 h | 35.7% |
| 8 h | 44.0% |
| 24 h | 61.1% |

The fermentation is interrupted after 24 hours and the desired fermentation product isolated as follows:

The broth is filtered. Aqueous phase and sediment are worked up separately. The aqueous phase is stirred out twice with 40 l of methylene chloride each time, the sediment is shaken out twice with 5 l of methylene chloride each time. The separated solvent phase is dewatered over Na₂SO₄ and concentrated under reduced pressure. It gives 248 g of crude extract. This crude extract is distilled at 81°–84°/14–15 Torr (bath temperature 105°–115° C.). There are obtained 107.8 g of product which, according to gas chromatogram, consists of to 95% of (S)-dihydro-3-methyl-2(3H)-furanone and has an optical rotation $\alpha_D = -20.7$ (2% in ethanol). In the NMR spectrum of the product, recorded with the addition of chiral shift reagents, only the one enantiomer (S-configuration) is observable.

EXAMPLE 2

Transformation of different educts to (S)-dihydro-3-methyl-2(3H)-furanone by Geotrichum candidum The microorganism is cultivated in the same manner to that which was described in Example 1.

In the case of the transformation experiments the following substrates are employed:

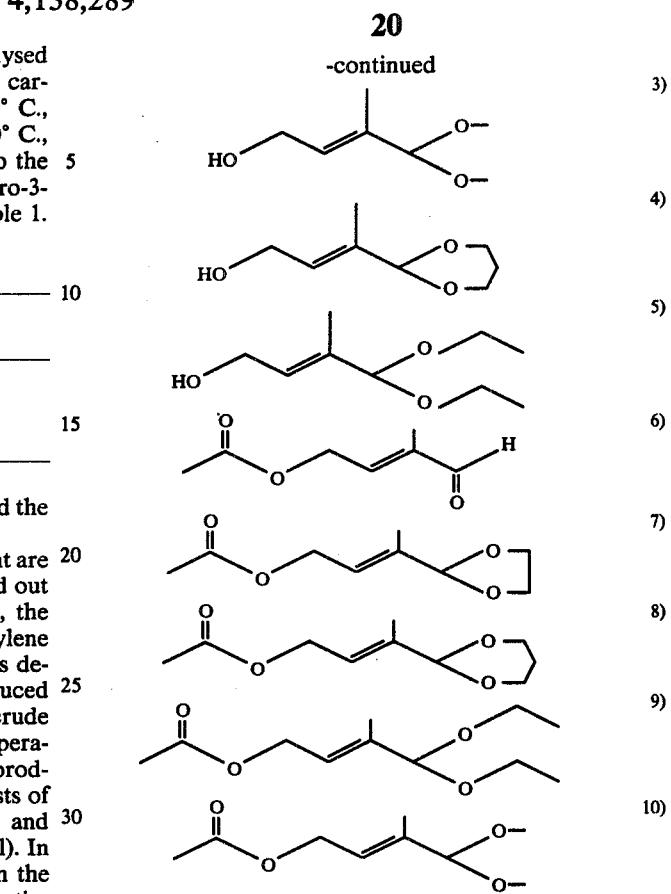

The transformation experiments are performed as follows: 5 g of biomass (Geotrichum candidum CBS 233.76) are suspended in 45 ml of sterile transformation medium which has the following composition:

| | | |
|---|---|---|
| D(+)-glucose (monohydrate) | 50 g | in 1 l of |
| KH₂PO₄ | 8 g | deionised |
| Na₂HPO₄ | 1.3 g | water (pH 6) |

The educt in a concentration of 1 or 2 g/l (see Table) is now added and the batch incubated at 30° during 7 days on a rotary shaking machine (260 r/min) in a thermostatised room. After 1 and 7 days, a sample of 10 ml of removed and extracted twice with methylene chloride. The solvent phase is separated, dried over Na₂SO₄ and concentrated under reduced pressure. The residue is taken up in so much dioxan that in relation to the educt employed there results a 1% solution which is subsequently analysed gas-chromatographically. The results are contained in the following Table.

Table

| Educt | Educt concentration in g/l | in % according to gas chromatogram (G) Fermentation time 1 day | Fermentation time 7 days |
|---|---|---|---|
| 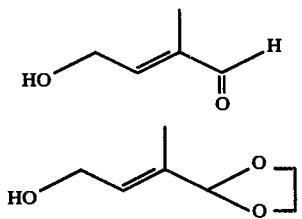 | 1 | 15 | 33 |

Table -continued

| Educt | Educt concentration in g/l | Fermentation time 1 day | Fermentation time 7 days |
|---|---|---|---|

(values for column "in % according to gas chromatogram (G)" showing lactone product with CH₃)

| Structure | g/l | 1 day | 7 days |
|---|---|---|---|
| HO–CH₂–CH=C(CH₃)–CH(–O–)(–O–) (dioxirane) | 2 | 40 | 75 |
| HO–CH₂–CH=C(CH₃)–CH(OMe)₂ | 2 | 32 | 74 |
| HO–CH₂–CH=C(CH₃)–CH(–OCH₂CH₂O–) (dioxolane) | 2 | 89 | 95 |
| HO–CH₂–CH=C(CH₃)–CH(OEt)₂ | 2 | 74 | 94 |
| AcO–CH₂–CH=C(CH₃)–CHO | 1 | 20 | 79 |
| AcO–CH₂–CH=C(CH₃)–CH(–O–)(–O–) | 1 | 24 | 45 |
| AcO–CH₂–CH=C(CH₃)–CH(–OCH₂CH₂O–) | 2 | 79 | 88 |
| AcO–CH₂–CH=C(CH₃)–CH(OEt)₂ | 2 | 76 | 89 |
| AcO–CH₂–CH=C(CH₃)–CH(OMe)₂ | 1 | 17 | 55 |

EXAMPLE 3

Transformation of ethyl-trans-4,4-dimethoxy-3-methyl-crotonate by pressed yeast

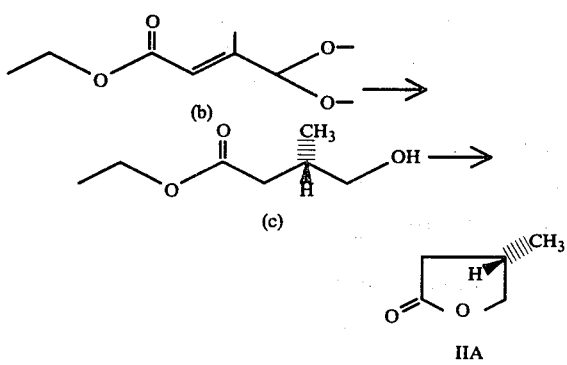

A clean, but not sterilised, fermenter with 31 l total volume is charged with the following ingredients:

| | | |
|---|---|---|
| Deionised water | 9.9 | l |
| Pressed yeast | 1.1 | kg |
| Sugar | 0.55 | kg |
| Ethyl-4,4-dimethoxy-3-methylcrotonate (b) | 133 | g |
| Polypropyleneglycol monobutyl ether | 10 | ml |

The fermentation is carried out under the following conditions:

| | |
|---|---|
| Temperature | 30° (thermostatically regulated) |
| Stirring frequency | 1000 r/min |
| Air-flow rate | 600 l/h |
| pH | 3.4–3.8 (no pH-regulation) |
| Fermentation time | 56 h |

After 16, 24, 40, 48 and 56 h, samples of 10 ml are removed and extracted twice with methylene chloride. The solvent phase is separated, dried over Na₂SO₄ and concentrated under reduced pressure. The residue is taken up in so much dioxan that in relation to the educt employed there results a 1% solution and subsequently analysed gas-chromatographically. The results are compiled in the following Table:

| Fermentation time | Composition of the extract in % | | | |
|---|---|---|---|---|
| | ethyl 2-methyl-4,4-dialkoxy-crotonate | ethyl 2-methyl-4-hydroxy-crotonate | ethyl (S)-3-methyl-4-hydroxybutyrate | (S)-dihydro-4-methyl-2(3H)-furanone |
| 16 h | 23.8 | 40.6 | 34.3 | 0.3 |
| 24 h | 11.9 | 43.4 | 42.7 | 0.3 |
| 40 h | 3.7 | 43.3 | 49.1 | 0.3 |
| 48 h | 1.8 | 44.4 | 50.1 | 0.7 |
| 56 h | 0.5 | 46.9 | 49.2 | 1.0 |

The fermentation is interrupted after 56 h and the desired fermentation product isolated in accordance with the following:

The broth is saturated with NaCl and continuously extracted during 4 days with diethyl ether. The solvent is separated, dried over Na$_2$SO$_4$ and removed further under reduced pressure. There are obtained 122 g of crude extract which contains for the most part (S)-3-methyl-4-hydroxy-butyric acid ethyl ester. This substance can be purified chromatographical (over silicagel which has been deactivated with 0.5% NH).

EXAMPLE 4

Hydrolysis of the (S)-3-methyl-4-hydroxy-butyric acid ethyl ester and purification of the resulting (S)-dihydro-4-methyl-2(3H)-furanone The crude extract obtained in accordance with Example 3 is treated with 100 mg of p-toluenesulphonic acid and distilled in a nitrogen atmosphere under reduced pressure. The (S)-dihydro-4-methyl-2(3H)-furanone formed during the distillation distills at 86°–88° C./14 Torr (bath temperature 125°–140°). There are obtained 26.2 g of product which, according to GC, contains 93% of (S)-dihydro-4-methyl-2(3H)-furanone and has an optical rotation of −21° (4% in methanol). The optical purity of the (S)-dihydro-4-methyl-2(3H)-furanone can be demonstrated, after conversion of the lactone into the corresponding bromo ester

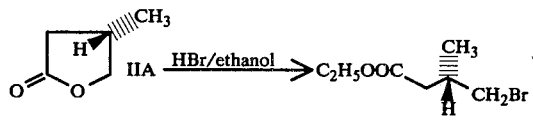

on the basis of the NMR spectrum, recorded with the addition of a chiral shift reagent (Eu(HFC)$_3$).

The yield of isolated, optically pure (S)-dihydro-4-methyl-2(3H)-furanone is 34.4% of the theoretically possible amount of product.

EXAMPLE 5

Transformation of ethyl-trans-4,4-dimethoxy-3-methyl-crotonate with continuous supply of substrate. Biocatalyst. Pressed yeast.

Two transformation experiments A and B are carried out in clean, but not sterilised, small fermenters (absolute volume 5 l) with the continuous supply of substrate (ethyl-trans-4,4-dimethoxy-3-methyl-crotonate). In each case the fermenter is charged with the following ingredients:

| | |
|---|---|
| Deionised water (not sterile) | 4.5 l |
| Crystalline sugar | 250 g |
| Pressed yeast | 500 g |

Both transformations are carried out under the following conditions.

| | |
|---|---|
| temperature | 30° C |
| Stirring frequency | 1000 r/min |
| air-flow rate | 600 l/min |
| pH | 3.0–4.3 (no pH - regulation |

The substrate is continuously pumped in at a supply rate of about 7.5 ml/h. In the case of A the substrate is fed for 10 hours and a final concentration of 16g/l achieved. In the case of B substrate is pumped in for 22 hours, and the final concentration amounts to 33 g/l.

Further, in experiment B 100 g sugar is subsequently added after 17 hours of fermentation.

10ml Polypropyleneglycol-monobutyl ether are added to prevent the formation of foam.

The progress of fermentations A and B is monitored by gas chromatographical analysis in accordance with Example 3.

Reactions A and B are largely completed after 20 and 46 hours respectively. After these fermentation times the GC analyses show the following percentage composition of the extract:

| Experiment | Fermentation time | Substrate: Final concentration | Composition of the extract in % according to GC | | | | |
|---|---|---|---|---|---|---|---|
| | | | ethyl 2-methyl-4,4-dialkoxy-crotonate | ethyl 2-methyl-4-oxo-crotonate | ethyl 2-methyl-4-hydroxy-crotonate | ethyl (S)-3-methyl-4-hydroxybutyrate | (S)-dihydro-4-methyl-2(3H)-furanone |
| A | 20 h | 16 g/l | 5,6 | 0,4 | 37,3 | 53,4 | 1,6 |
| B | 46 h | 33 g/l | 17,5 | 6,8 | 30,0 | 40,2 | 2,0 |

The isolation of the saturated hydroxyesters and the conversion to (S)-dihydro-4-methyl-2(3H)-furanone is effected according to Examples 3 and 4. There are isolated 18.2 g from batch A and 23.0 g from batch B of optically pure (S)-dihydro-4-methyl-2(3H)-furanone.

EXAMPLE 6

The transformation experiments are conducted in the same manner to that which is described in Example 2. However, 5 g of pressed yeast are employed as the biocatalyst. The following Table shows the results:

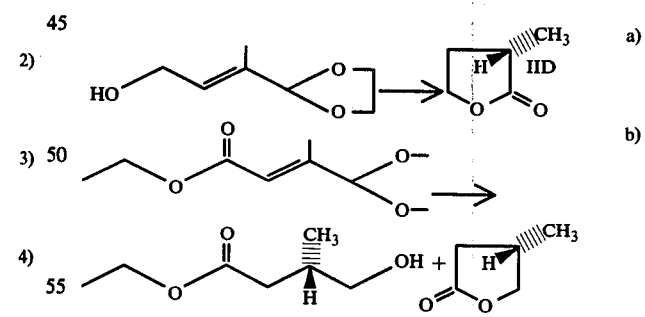

| Educt | Educt concentration g/l | 1 d | 3 d | 7 d |
|---|---|---|---|---|
| (structure 1) | 1 | 14 | 26 | 36 |
| (structure 2) | 1 | 69 | 75 | 63 |
| (structure 3) | 2 | 61 | 66 | 58 |
| (structure 4) | 2 | — | 12 | 10 |
| (structure 5) | 2 | — | 5 | 5 |
| (structure 6) | 1 | 5 | 22 | 45 |
| (structure 7) | 2 | 4 | 17 | 34 |

Transformation of different educts to optically active intermediate products which can be converted into (S)-dihydro-4-methyl-2(3H)-furanone. Pressed yeast as the biocatalyst In the case of the transformation experiments there are employed the following substrates

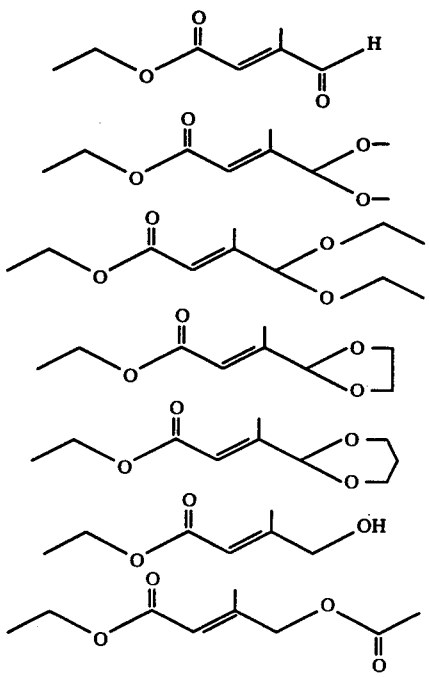

1)
2)
3)
4)
5)
6)
7)

EXAMPLE 7

Transformation of trans-3-(1,3-dioxolan-2-yl)-2-buten-1-ol and ethyl-trans-4,4-dimethoxy-3-methylcrotonate by different microorganisms At least 70 arbitrarily chosen microorganisms are tested for their capability to bring about the following transformation reactions a)

b)

The microorganisms are chosen from the following groups:

1. Eucaryontes
   1.1. Yeasts of the genera:  Candida
                                Kloeckera
                                Rhodotorula
                                Saccharomyces
                                Torulopsis
   1.2. Fungi of the genera:   Absidia
                                Aspergillus
                                Colletotrichum
                                Cunninghamella
                                Curvularia -continued

| | |
|---|---|
| | Cylindrocarpon |
| | Endomyces |
| | Fusarium |
| | Gibberella |
| | Gliocladium |
| | Hypomyces |
| | Mucor |
| | Penicillium |
| | Phycomyces |
| | Rhizopus |
| | Trichothecium |
| 2. Procaryontes | |
| 2.1. Actinomycetes of the genera: | Actinomyces |
| | Mycobacterium |
| | Nocardia |
| | Proactinomyces |
| | Streptomyces |
| 2.2. Gram-positive bacteria of the genera: | Arthrobacter |
| | Bacillus |
| | Micrococcus |
| | Pediococcus |
| | Propionibacterium |
| | Sarcina |
| | Steptococcus |
| 2.3. Gram-negative bacteria of the genera | Azotobacter |
| | Klebsiella |
| | Pseudomonas |
| | Serratia |
| | Vibrio |

The microorganisms are inoculated into 50 ml of a complex cultivation medium with the use of the customary microbiological working procedures and incubated on a shaking machine at 30° C. during 48–72 h. The medium is composed in accordance with the following:

| | | |
|---|---|---|
| $KH_2PO_4$ | 3.7 g | in one liter of deionised water |
| $Na_2HPO_4$ | 7.0 g | |
| Yeast extract (Difco) | 10 g | |
| D(+)-glucose (monohydrate) | 20 g | |

After 48–72 h there are again added to each 50 ml batch 0.5 g of D(+)-glucose (monohydrate) (10 g/l) as well as 50 mg of trans-3-(1,3-dioxolan-2-yl)-2-buten-1-ol or trans-1-ethyl-4,4-dimethoxy-3-methylcrotonate (1 g/l). The incubation is continued under the same condition for one week long. After one and after 7 days, 10 ml in each case of the cell suspension of all batches is extracted twice with methylene chloride. The organic phase is dried over $Na_2SO_4$ and concentrated at 40° C. under reduced pressure. The residue is taken up in 1 ml of dioxan and analysed gas-chromatographically. The results are compiled in the following Tables. In these Tables − signifies no conversion to the desired product ± signifies that there are detected only traces of the desired product (conversion <5%)

+ signifies that the crude extract contains at least 5% of the desired product.

| | YEASTS | | | |
|---|---|---|---|---|
| | Transformation reaction a) | | Transformation reaction b) | |
| Microorganism | 1 day | 7 days | 1 day | 7 days |
| Candida albicans | + | + | ± | ± |
| Candida guillermondii | + | + | ± | ± |
| Candida utilis 621 CBS | ± | ± | + | ± |
| Kloeckera brevis, strain 1 | − | ± | + | + |
| Kloeckera brevis, strain 2 | ± | − | + | + |
| Rhodotorula rotundata | + | + | ± | ± |
| Saccharomyces carlsbergensis | ± | ± | + | + |
| Saccharomyces cerevisiae, strain 1 | ± | ± | + | + |
| Saccharomyces cerevisiae, strain 2 | ± | ± | + | + |
| Saccharomyces cerevisiae, strain 3 | ± | + | + | + |
| Saccharomyces cerevisiae, ellipsoides - 9896 ATCC | ± | ± | + | + |
| Torulopsis apicola PRL No. 123-64 | + | + | + | ± |
| Torulopsis rotundata NRRL 1402 | + | + | − | ± |

| | FUNGI | | | |
|---|---|---|---|---|
| | Transformation reaction a) | | Transformation reaction b) | |
| Microorganism | 1 day | 7 days | 1 day | 7 days |
| Absidia regneri Lendner | ± | + | + | ± |
| Aspergillus clavatus | + | + | ± | ± |
| Aspergillus fischeri | + | ± | ± | ± |
| Aspergillus flavus | + | − | − | ± |
| Aspergillus fumigatus | + | + | ± | ± |
| Aspergillus niger | ± | + | + | + |
| Aspergillus ochraceus 12337 ATCC | + | + | − | ± |
| Aspergillus wentii Wehmer | ± | − | ± | ± |
| Colletotrichum gloeosporioides | ± | − | ± | + |
| Cunninghamella blakesleeana | + | ± | + | + |

-continued

FUNGI

| Microorganism | Transformation reaction a) 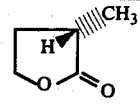 | | Transformation reaction b) 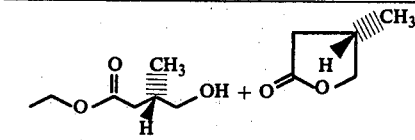 | |
|---|---|---|---|---|
| | 1 day | 7 days | 1 day | 7 days |
| *Curvularia lunata* NRRL 2380 | + | + | ± | ± |
| *Cylindrocarpon radicicola* 11011 ATCC | + | − | ± | ± |
| *Endomyces fibuliger* 2521 CBS | ± | + | ± | ± |
| *Fusarium culmorum* | | | ± | ± |
| *Fusarium solani* 12823 ATCC | | | ± | ± |
| *Gibberella fujikuroi* | + | − | + | + |
| *Gliocladium roseum* | ± | + | + | + |
| *Hypomyces rosellus* | | | ± | ± |
| *Mucor circinelloides* | | | + | + |
| *Mucor corymbifer* | + | + | ± | ± |
| *Mucor griseo-cyanus* | + | + | + | + |
| *Mucor hiemalis* | + | + | | |
| *Mucor parasiticus* 6476 ATCC | + | + | + | + |
| *Mucor spinosus* 2604 ETH | + | + | | |
| *Penicillium griseofulvum* 11885 ATCC | | | ± | ± |
| *Penicillium notatum* 832 CBS | + | + | ± | − |
| *Penicillium novae-zeelandiae* 10473 ATCC | + | − | ± | + |
| *Penicillium viride* 2603 ETH | + | + | ± | ± |
| *Phycomyces blakesleeanus* | ± | + | ± | + |
| *Rhizopus arrhizus* 11145 ATCC | + | + | + | + |
| *Rhizopus circinans*, strain 1 | ± | + | + | + |
| *Rhizopus circinans*, strain 2 | − | ± | + | + |
| *Trichothecium roseum* 8685 ATCC | − | − | ± | + |

ACTINOMYCETES

| Microorganism | Transformation reaction a) 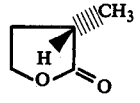 | | Transformation reaction b) 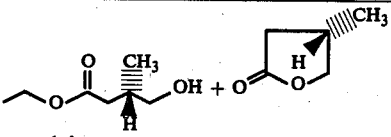 | |
|---|---|---|---|---|
| | 1 day | 7 days | 1 day | 7 days |
| *Actinomyces cellulosae* | − | − | ± | ± |
| *Mycobacterium butyricum* | ± | + | ± | + |
| *Mycobacterium phlei* | − | − | ± | ± |
| *Mycobacterium rhodochrous* 4277 ATCC | ± | + | ± | − |
| *Nocardia asteroides* 27042 ETH | − | − | ± | ± |
| *Nocardia brasiliensis* 27048 ETH | − | − | ± | ± |
| *Nocardia opaca* 33161 CBS | ± | ± | ± | − |
| *Proactinomyces restrictus* 15745 CBS | + | + | ± | ± |
| *Proactinomyces roseus* | ± | + | ± | − |
| *Streptomyces albus* 6860 ATCC | − | − | ± | ± |
| *Streptomyces fradiae* 10745 ATCC | + | + | ± | ± |
| *Streptomyces lavendulae* 11924 ATCC | − | − | ± | − |
| *Streptomyces rimosus* 10970 ATCC | ± | + | ± | ± |
| *Streptomyces venezuelae* 10595 ATCC | ± | − | ± | − |

BACTERIA gram-positive

| Microorganism | Transformation reaction a) 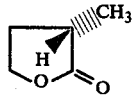 | | Transformation reaction b) 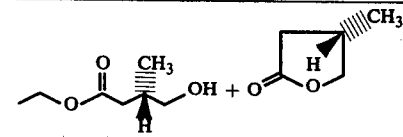 | |
|---|---|---|---|---|
| | 1 day | 7 days | 1 day | 7 days |
| *Arthrobacter simplex* 6946 ATCC | − | − | ± | ± |
| *Bacillus megatherium* | − | ± | ± | ± |
| *Bacillus sphaericus* 12300 ATCC | − | ± | ± | ± |
| *Bacillus subtilis* 6633 ATCC | + | + | ± | ± |
| *Micrococcus lysodeikticus* 4638 ATCC | + | + | ± | ± |
| *Pediococcus cerevisiae* 8042 ATCC | ± | + | ± | ± |
| *Propionibacterium shermanii* | + | + | − | ± |
| *Sarcina lutea* 8340 ATCC | − | ± | ± | ± |
| *Streptococcus faecalis* 9790 ATCC | + | + | ± | ± |

-continued

| | BACTERIA gram-positive | | | |
|---|---|---|---|---|
| | Transformation reaction a) | | Transformation reaction b) | |
| Microorganism | 1 day | 7 days | 1 day | 7 days |
| *Streptococcus lactis* | + | + | ± | ± |

| | BACTERIA gram-negative | | | |
|---|---|---|---|---|
| | Transformation reaction a) | | Transformation reaction b) | |
| Microorganism | 1 day | 7 days | 1 day | 7 days |
| *Azotobacter indicus* 9540 ATCC | − | − | ± | + |
| *Klebsiella pneumoniae* | − | − | ± | ± |
| *Pseudomonas fluorescens* 13430 ATCC | + | + | ± | − |
| *Pseudomonas testosteroni* 11996 ATCC | − | − | ± | ± |
| *Serratia marcescens* | ± | + | ± | ± |
| *Vibrio metschnikovii* 7708 ATCC | ± | + | − | ± |

The results can be compiled as follows:

-continued

| Transformation reaction | Number of tested strains | No desired product observed | ± less than 5% product | + at least 5% product |
|---|---|---|---|---|
| (image) | 71 | 11 (15,5 %) | 15 (21,1 %) | 45 (63,4 %) |
| (image) | 74 | 0 | 48 (64,9 %) | 26 (35,1 %) |

EXAMPLE 8

Manufacture of the optically active half ester 2-methyl-3-ethoxycarbonyl-propionic acid

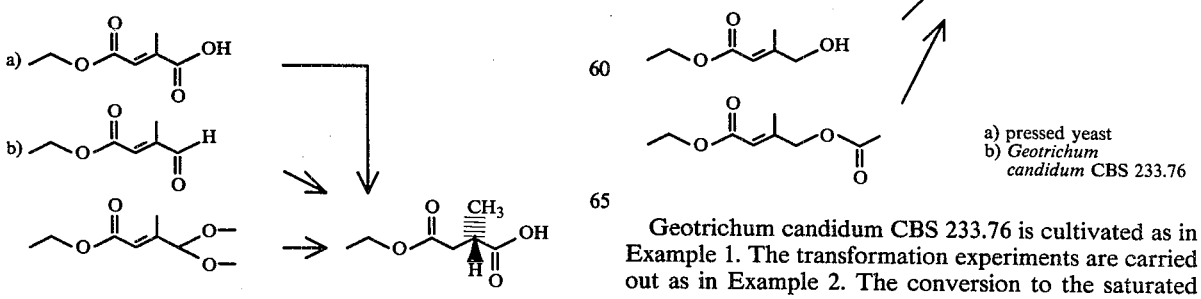

a) pressed yeast
b) *Geotrichum candidum* CBS 233.76

Geotrichum candidum CBS 233.76 is cultivated as in Example 1. The transformation experiments are carried out as in Example 2. The conversion to the saturated half ester (according to GC) is tabulated hereinafter for fermentation times of 1, 3 and 7 days:

pressure. There are obtained 586 mg of ethyl-(S)-3-methyl-4-hydroxybutyrate as a colourless oil.

| Educt | Educt concentration in g/l | Microorganism | Product (ethyl-(S)-3-methyl-4-hydroxybutyrate) in % | | |
|---|---|---|---|---|---|
| | | | 1 day | 3 days | 7 days |
| ethoxycarbonyl methylbutenoic acid | 1 | Pressed yeast | 70 | 92 | 76 |
| ethoxycarbonyl methylbutenal | 1 | Geotrichum | 72 | 82 | 78 |
| ethoxycarbonyl methylbutenal dimethyl acetal | 1 | candidum | 1 | 14 | 38 |
| ethoxycarbonyl methylbutenal diethyl acetal | 2 | CBS | 7 | 66 | 84 |
| ethoxycarbonyl methylbutenol | 1 | 233.76 | 80 | 75 | 75 |
| ethoxycarbonyl methylbutenyl acetate | 2 | | 41 | 77 | 79 |

EXAMPLE 9

Conversion of (S)-2-methyl-3-ethoxycarbonyl-propionic acid into (S)-dihydro-4-methyl-2(3H)-furanone 819 mg of the optically active half ester obtained in accordance with Example 7 is dissolved in a nitrogen atmosphere in 6 ml of absolute tetrahydrofuran and cooled to 0° to −10°. After addition of 3 ml of trimethylborate and 10.3 ml of a 5% complex of $BH_3 \cdot S(CH_3)_2$ in tetrahydrofuran (dropwise), the reaction mixture is stirred at −10° to 0° for 50 minutes in an argon atmosphere. After cautious addition of 20 ml of methanol, the mixture is evaporated at 40° under reduced pressure. The residue is dissolved in dichloromethane and shaken successively with 30 ml of saturated aqueous sodium bicarbonate solution and twice with 20 ml of aqueous common salt solution. The aqueous phase is extracted three times with dichloromethane. The combined organic phases are dried over magnesium sulphate, filtered and evaporated under reduced The ethyl-(S)-3-methyl-4-hydroxybutyrate obtained is heated under reflux conditions with a trace of p-toluenesulphonic acid in methanol for 3 hours. There is obtained (S)-dihydro-4-methyl-2(3H)-furanone which boils at about 50°/0.1 Torr.

EXAMPLE 10

Transformation of trans-1,1,4-trimethoxy-2-methyl-2-butene and trans-4-methoxy-2-methyl-buten-1-ol or -1-ol-acetate, trans-2-(3-methoxy-1-methyl propenyl)-1,3-dioxolan or trans-4-methoxy-2-methyl-croton aldehyde by pressed yeast or Geotrichum candidum As the microorganisms there are used commercial pressed yeast or Geotrichum candidum CBS 233.76 (cultivation as in Example 1). As the substrate there are employed 0.2% of the following educts a, b and c. The transformation experiments are carried out as in Example 2. There thereby result depending on the choice of the microorganism the following main products:

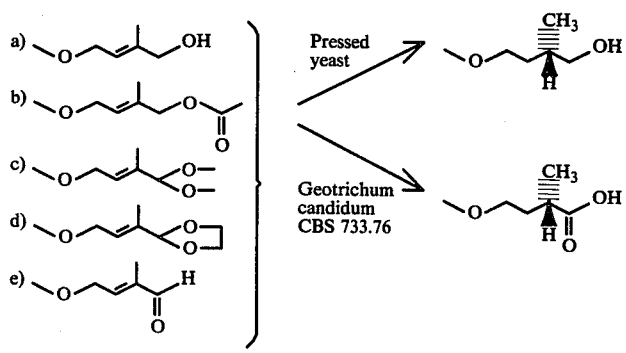

The conversion to these products (according to GC = gas chromatogram) are tabulated hereinafter for fermentation times of 1, 3 and 7 days:

| Educt | Microorganism | Fermentation time in days | [product 1: ~O~~CH3~~OH with H] in % acc. to GC | [product 2: ~O~~CH3~~OH with H, =O] in % acc. to GC |
|---|---|---|---|---|
| ~O~~~~OH | Pressed yeast | 1 | 17 | 0 |
|  |  | 3 | 36 | 7 |
|  |  | 7 | 26 | 32 |
|  | Geotrichum candidum CBS 233.76 | 1 | 1 | 42 |
|  |  | 3 | 0 | 51 |
|  |  | 7 | 0 | 64 |
| ~O~~~~O-C(=O)- | Pressed yeast | 1 | 13 | 0 |
|  |  | 3 | 32 | 5 |
|  |  | 7 | 24 | 25 |
|  | Geotrichum candidum CBS 233.76 | 1 | 5 | 34 |
|  |  | 3 | 1 | 39 |
|  |  | 7 | 0 | 45 |
| ~O~~~~(O-)(O-) | Pressed yeast | 1 | 32 | 0 |
|  |  | 3 | 54 | 2 |
|  |  | 7 | 49 | 27 |
|  | Geotrichum candidum CBS 233.76 | 1 | 0 | 86 |
|  |  | 3 | 0 | 91 |
|  |  | 7 | 0 | 91 |
| ~O~~~~(O-)(O-) cyclic | Pressed yeast | 1 | 34 | 0 |
|  |  | 3 | 48 | 0 |
|  |  | 7 | 38 | 36 |
|  | Geotrichum candidum CBS 233.76 | 1 | 20 | 66 |
|  |  | 3 | 0 | 94 |
|  |  | 7 | 0 | 97 |
| ~O~~~~CHO | Pressed yeast | 1 | 21 | 0 |
|  |  | 3 | 43 | 0 |
|  |  | 7 | 31 | 39 |
|  | Geotrichum candidum CBS 233.76 | 1 | 37 | 0 |
|  |  | 3 | 1 | 71 |
|  |  | 7 | 0 | 82 |

EXAMPLE 11

11.0 g (0.11 mol) of (S)-dihydro-4-methyl-2(3H)-furanone are added dropwise within the course of 10 min. while stirring at 0° to 110 ml of a freshly manufactured ethanolic hydrogen bromide solution (about 8-N). The reaction mixture is subsequently stirred further at room temperature for two hours. For the working-up the reaction mixture is poured on to ice, diluted with water to about 1 liter and shaken out twice with chloroform. The combined organic phases are washed neutral first with water, then with saturated sodium bicarbonate solution and dried over sodium sulphate. After removal of the chloroform on the rotary evaporator, the colourless ethyl-(S)-4-bromo-3-methylbutyrate distills in the water-jet vacuum at 90°–92° in a yield of 18.5 g (80%); $[\alpha]_D^{20} = 2.3°$ (c = 4.0, CHCl$_3$).

To 204 ml (C.204 mol) of a 1-M solution of diisobutylaluminium hydride are added dropwise in an argon atmosphere at 0° while stirring within the course of 15 min. 17.8 g (0.085 mol) of ethyl-(S)-4-bromo-3-methylbutyrate. The excess of the reduction agent is decomposed by dropwise addition of methanol at 0°. Subsequently, the reaction mixture is poured on to ice and acidified by addition of 2-N aqueous sulphuric acid, the precipitated aluminium hydroxide going partially into solution. The (S)-4-bromo-3-methyl-1-butanol formed is taken up in ether by shaking several times. The combined ether phases are washed neutral first with saturated sodium bicarbonate solution, then with saturated common salt solution and dried over sodium sulphate. After removal of the solvent on the rotary evaporator, the yield amounts to 14.0 g (98%); the product can be used further without distillation. For analytical purposes a sample is distilled in the bulb-tube at 60°/0.04 Torr; $[\alpha]_D^{20} = -2.0°$ (c = 3.3, CHCl$_3$).

14 g (0.084 mol) of (S)-4-bromo-3-methyl-1-butanol are treated dropwise at 0° with 50 ml of freshly distilled 3,4-dihydro-2H-pyran. The reaction mixture is subsequently stirred at 0° for 1 hour. Excess 3,4-dihydro-2H-pyran is removed at 35° on the rotary evaporator. For the complete removal of the 3,4-dihydro-2H-pyran chloroform is repeatedly added, in each case followed by distillation on the rotary evaporator. The crude product [(S)-4-bromo-3-methylbutoxy]-tetrahydro-2H-pyran is distilled at 75°/0.03 Torr in a yield of 17.5 g (83%); $[\alpha]_D^{20} = +3.4°$ (c = 4.0, CHCl$_3$).

4.7 g (0.202 mol) of magnesium shavings in a 3-necked flask under an argon atmosphere and provided with a calcium chloride tube are activated by addition of 2.0 ml of methyl iodide. After 5 minutes, the methyl iodide is removed and the magnesium washed several times with absolute tetrahydrofuran. To the activated magnesium is added dropwise a solution of 44 g (0.175 mol) of 2-[(S)-4-bromo-3-methylbutoxy]-tetrahydro-2H-pyran in 50 ml of absolute tetrahydrofuran at such a rate that the solvent just boils. Where the Grignard reaction does not start itself, it is warmed to 85° with the oil bath. After completed addition of 2-[(S)-4-bromo-3-methylbutoxy]-tetrahydro-2H-pyran, the mixture is stirred at 85° for so long (0–15 min.) until only traces of 2-[(S)-4-bromo-3-methylbutoxy]-tetrahydro-2H-pyran are still present in accordance with gas-chromatographical analysis. The solution obtained is cooled to −78° and treated dropwise with 21.2 g (0.0875 mol) of 3-methyl-1-butanol-p-toluenesulphonate followed by 3.6 ml of a 0.1 molar solution of Li$_2$CuCl$_4$ in absolute tetrahydrofuran. This reaction mixture is stirred at −78° during 10 min. then at 0° for 2 hours and subsequently at room temperature for a further 14 hours. For the working up of the 2-[(R)-3,7-dimethyloctanoxy]-tetrahydro-2H-pyran obtained the mixture is poured on to ice and brought to pH 5–6 with 2-N sulphuric acid. By threefold extraction with ether and removal of the solvent on the rotary evaporator there is obtained a mixture of (R)-3,7-dimethyl-1-octanol and 2-[(R)-3,7-dimethyloctanoxy]-tetrahydro-2H-pyran. This mixture is treated portionwise in 100 ml of methanol at 0° with a total of 100 ml of 7-N aqueous hydrochloric acid. After 2-hours stirring at room temperature, the mixture is neutralised with dilute aqueous caustic soda and extracted with ether. After chromatography on silicagel, deactivated with 0.5% ammonia, with pentane/ether (4:1), there are obtained 10.6 g (76% based on 3-methyl-1-butanol-p-toluenesulphonate employed) of pure (R)-3,7-dimethyl-1-octanol. B.p. 58°-59°/0.05 Torr; $[\alpha]_D^{20} = +4.0$ (c = 1.03, CHCl$_3$).

The (R)-3,7-dimethyl-1-octanol can also be obtained as follows:

1.26 g (5 mmol) of 2-[(S)-4-bromo-3-methylbutoxy]-tetrahydro-2H-pyran are added dropwise within the course of one minute at 0° in an argon atmosphere and while stirring to a Grignard solution (manufactured in analogy to the above described magnesium derivative of 2-[(S)-4-bromo-3-methylbutoxy]-tetrahydro-2H-pyran) from 0.3 g (12.4 mmol) of magnesium and 1.51 g (10 mmol) of 1-bromo-3-methylbutane in 25 ml of absolute tetrahydrofuran. Subsequently, 0.3 ml of a 0.1-M solution of Li$_2$CuCl$_4$ in tetrahydrofuran is added and the reaction mixture is stirred further at 0° for 3 hours. The working-up as well as the hydrolysis of 2-[(R)-3,7-dimethyloctanoxy]-tetrahydro-2H-pyran to (R)-3,7-dimethyl-1-octanol is effected in the manner given above. The yield of (R)-3,7-dimethyl-1-octanol amounts to 0.56 g (71%) after bulb-tube distillation at 95°/14 Torr; $[\alpha]_D^{20} = +4.0$ (c = 1.03, CHCl$_3$).

A solution of 6.5 g (41 mmol) of (R)-3,7-dimethyl-1-octanol and 7.8 g (41 mmol) of p-toluenesulphonyl chloride in 50 ml of absolute chloroform is treated at 0° with 7.9 g (0.1 mol) of absolute pyridine. The mixture is subsequently stirred at 4° for 20 hours. For the working-up the mixture is poured on to 500 g of ice and extracted three times with chloroform. The combined organic phases are washed first with cold 1-N hydrochloric acid, then with saturated aqueous sodium bicarbonate solution and subsequently with saturated aqueous common salt solution. After drying over potassium carbonate and removal of the solvent under reduced pressure, the crude product is chromatographed on 300 g of silicagel with benzene. There are obtained 11.4 g (89%) of (R)-3,7-dimethyl-1-octanol p-toluenesulphonate; $[\alpha]_D^{20} = +2.0$ (c = 4.0, benzene).

A Grignard solution from 2 g of magnesium and 18.3 g (72.6 mmol) of 2-[(S)-4-bromo-3-methylbutoxy]-tetrahydro-2H-pyran in 50 ml, manufactured in the manner given hereinafter, is treated at −78° with 11.4 g (36.3 mmol) of (R)-3,7-dimethyl-1-octanol-p-toluenesulphonate and 3 ml of a 0.1 molar solution of Li$_2$CuCl$_4$ in tetrahydrofuran. The working-up as well as the hydrolysis of the tetrahydro-2-{[(3R 7R)-3,7,11-trimethyldodecyl]-oxy}-2H-pyran to (3R,7R)-3,7,11-trimethyl-1-dodecanol is effected in analogy to the following description for the working-up and hydrolysis of 2-[(R)-3,7-dimethyl-octanoxy]-tetrahydro-2H-pyran. The (3R, 7R)-3,7,11-trimethyl-1-dodecanol distills at 114°/0.04 Torr in a yield of 7.0 g (84% based on based on (R)-3,7-dimethyl-1-octanol-p-toluenesulphonate); $[\alpha]_D^{20} = +3.7°$ (c = 1.015, n-octane).

The mixture of tetrahydro-2-{[(3R, 7R)-3,7,11-trimethyldodecyl]-oxy}-2H-pyran and (3R, 7R)-3,7,11-trimethyl-1-dodecanol obtained in the course of the working-up can be separated chromatographically (silicagel deactivated with 0.5% aqueous ammonia; elution agent: toluene). The tetrahydro-2-{[(3R,7R)-3,7,11-trimethyldodecyl]-oxy}-2H-pyran has an optical rotation value of $[\alpha]_D^{20} = +2.33°$ (c = 4.0, chloroform).

The (3R,7R)-3,7,11-trimethyl-1-dodecanol can likewise be manufactured as follows:

5.65 g (31.8 mmol) of N-bromosuccinimide are added portionwise while stirring to a solution of 5 g (31.6 mmol) of (R)-3,7-dimethyl-1-octanol and 9.05 g (34.5 mmol) of triphenylphosphine in 20 ml of methylene chloride. The temperature is held below 25° by occasional cooling of the reaction vessel. After 30-minutes stirring at room temperature, the solvent is removed on the rotary evaporator. The residue is washed out several times with n-hexane, then filtered and again rinsed with n-hexane. The combined n-hexane phases are concentrated on the rotary evaporator and the crude product is chromatographed on 200 g of silicagel with n-hexane. Distillation in the bulb-tube at 105°/15 Torr gives 6.1 g (87%) of (R)-1-bromo-3,7-dimethyloctane; $[\alpha]_D^{20} = -5.0$ (c = 0.82, CHCl$_3$).

A Grignard solution is prepared in the manner described above in Example 10 from 0.3 g (12.4 mmol) of magnesium and 2.54 g (11.5 mmol) of (R)-1-bromo-3,7-dimethyloctane in 10 ml of absolute tetrahydrofuran. To this solution are added dropwise at 0° 1.45 g (5.57 mmol) of 2-[(S)-4-bromo-3-methylbutoxy]-tetrahydro-2H-pyran followed by 0.3 ml. of a 0.1 molar solution of Li$_2$CuCl$_4$ in tetrahydrofuran. This reaction mixture is stirred at 0° for 3 hours. The working-up as well as hydrolysis of the tetrahydro-2-{[(3R,7R)-3,7,11-trimethyldodecyl]-oxy}-2H-pyran obtained to (3R,7R)-3,7,11-trimethyl-1-dodecanol is effected in the manner described above in Example 10. The yield of (3R,7R)-3,7,11-trimethyl-1-dodecanol amounts, after bulb-tube distillation at 90°-95°/0.05 Torr, to 0.5 g (43% based on 2-[(S)-4-bromo-3-methylbutoxy]-tetrahydro-2H-pyran); $[\alpha]_D^{20} = +3.9°$ (c = 1.05, n-octane).

3.1 g (13.6 mmol) of (3R,7R)-3,7,11-trimethyl-1-dodecanol are treated with 4.02 g (15.3 mmol) of N-bromosuccinimide and 2.62 g (14.7 mmol) of triphenylphosphine in 13 ml of methylene chloride according to the method described above in Example 10. After chromatography and distillation, there are obtained 3.54 g (90%) of (3R,7R)-bromo-3,7,11-trimethyldodecane. B.p. 90°/0.05 Torr; $[\alpha]_D^{20} = -3.6$ (c = 1.005, n-octane).

The (3R,7R)-1-bromo-3,7,11-trimethyldodecane obtained can be transformed into (2R,4'R,8'R)-α-tocopherol or (2R,4'R, 8'R)-α-tocopheryl acetate in accordance with Helv. Chem. Acta, volume 46 (1963), pages 650–675.

EXAMPLE 12

250 ml of about 11-N ethanolic hydrochloric acid are treated dropwise with 25.8 g of (S)-dihydro-3-methyl-2(3H)-furanone within the course of 10 minutes. The solution, which rapidly becomes dark, is stirred at room temperature for 10 seconds and subsequently extracted with methylene chloride. The organic phase is washed successively with saturated, aqueous bicarbonate solution and water, dried and concentrated under reduced pressure. After distillation of the residue at 15 Torr, there are obtained 39.7 (94%) of (S)-4-chloro-2-methyl-butyric acid ethyl ester as a colourless oil with boiling point 77°-78°. $[\alpha]_D^{20} = +26.9°$ (4.15% in ethanol).

A solution of 4.9 g (30.0 mmol) of (S)-4-chloro-2-methyl-butyric acid ethyl ester in 50 ml of n-hexane is treated dropwise at −70° under argon with 39 ml of a 20% solution of di-isobutylaluminium hydride in n-hexane. After completed reaction, the reaction mixture is treated at −30° with 5 ml of methanol, subsequently hydrolysed with ice-cold 1-N hydrochloric acid, extracted with ether, washed neutral with water, dried and evaporated under reduced pressure. (30° bath temperature). The residue is distilled at 15 Torr and 55°–58°. There are obtained 2.3 g (64%) of (S)-4-chloro-2-methylbutyraldehyde as a colourless liquid, $[\alpha]_D^{20} = -33.4°$ (4.21%, in CHCl$_3$).

A solution of 72.0 g of triphenylphosphine and 41.5 g of isoamyl bromide in 250 ml of dimethylformamide is heated under reflux conditions for 2 hours. The solvent is distilled off under reduced pressure, the residue crystallised twice from methanol/ether and finally held under strongly reduced pressure at 110° for 48 hours. There remains 70.3 g (61.9%) of 3-methylbutyl-triphenylphosphonium bromide, m.p. 153°–154° (uncorrected).

23.5 ml of n-butyllithium (about 2-M in n-hexane) are added dropwise under argon to a suspension of 20.4 g of 3-methylbutyl-trimethylphosphonium bromide in 80 ml of dry ether, a reaction temperature of about 20° being adhered to by slight cooling. Thereafter, the mixture is stirred at room temperature for a further 2 hours. The mixture is cooled to −10° and a solution of 5.4 g of (S)-4-chloro-2-methylbutyraldehyde in 5 ml of dry ether is added thereto. The separated precipitate is stirred for one hour without cooling bath, whereupon 100 ml of dimethylformamide are added dropwise at room temperature. The mixture is stirred at room temperature for 16 hours, hydrolysed on ice and extracted with ether. The ether phase is washed with water, dried and concentrated under reduced pressure. The residue is purified by adsorption on silicagel as well as on neutral aluminium oxide of the activities III and II (elution agent: n-hexane). After distillation under reduced pressure (13 mm Torr/90°), there are obtained 4.13 g (53%) of (S)-cis-1-chloro-3,7-dimethyl-4-octene. $[\alpha]_D^{20} = -32.6°$ (2.15% in chloroform).

A solution of 6.0 g of (S)-cis-1-chloro-3,7-dimethyl-4-octene and 10.8 g of triphenylphosphine in 40 ml of dimethylformamide is heated under reflux conditions for 2 hours. The mixture is concentrated under reduced pressure and washed with dry ether until only traces of triphenylphosphine are observable in the thin-layer chromatogram. The residue is dried firstly at 50° and later under strongly reduced pressure at room temperature overnight. There remain 9.0 g (60.0%) of a light brown glass. It is treated with 20 ml of dry ether and 10.5 ml of 2-M n-butyllithium solution are slowly added dropwise thereto. A dark red suspension has formed after several hours stirring under argon. At −10° there is slowly added dropwise a solution of 2.45 g of (S)-4-chloro-2-methylbutylraldehyde in 3 ml of dry ether. The mixture is stirred for 1 hour without cooling, then 50 ml of dry dimethylformamide added thereto at room temperature and the mixture stirred further overnight. The mixture is hydrolysed on ice, extracted with ether. The ether extract is washed free from dimethylformamide, dried and concentrated under reduced pressure. The residue is purified by adsorption on silicagel (elution agent: n-hexane) and distilled in the bulb-tube (85°, 0.05 Torr. There is obtained (3S,7S)-1-chloro-3,7,11-trimethyl-4-cis/trans-8-cis-dodecadiene. Yield 2.7 g (55%). $[\alpha]_D^{20} = -6.5°$ (4.07% in CHCl$_3$). The cis/trans ratio and therewith also the rotation value varies from batch to batch.

For the verification of the optical purity the compound obtained is hydrogenated on pre-hydrogenated platinum dioxide to (3R,7R)-1-chloro-3,7,11-trimethyl-dodecane; boiling point at 0.07 mm; 90°; = −1.2° (4.08% in CHCl$_3$), which is converted by heating with dry potassium acetate in dimethylformamide (4 hours at 170°). This ester is purified by adsorption on silicagel (elution agent: n-hexane/ether 4+1), then further reacted to (3R,7R)-3,7,11-trimethyl-1-dodecanol by stirring with 4-N aqurous caustic potash (30 min. at room temperature). The mixture is extracted, washed neutral, dried, concentrated, distilled in the bulb-tube (115°, 0.20 Torr) and there is obtained 3R,7R)-3,7,11-trimethyl-1-dodecanol in 94% yield (based on (3R,7R)-1-chloro-3,7,11-trimethyl-dodecane employed). The product has an optical rotation value of $[\alpha]_D^{20} = +3.7°$ (4.14% in n-octane) and is accordingly identical with authentic material.

The (3S,7S)-1-chloro-3,7,11-trimethyl-4-cis/trans-8-cis-dodecadiene can likewise be manufactured as follows:

A solution of 4.4 g of (S)-1-chloro-3,7-dimethyl-4-octene in 30 ml of isobutyl methyl ketone is stirred at 130° for 37 hours with 7.55 g of sodium iodide. A further 3.75 g of sodium iodide are added thereto and the mixture is stirred further for 4 hours. After cooling to room temperature, the mixture is diluted with ether, washed with water, dried and concentrated under reduced pressure. The residue is pre-purified by adsorption on silicagel (elution agent: n-hexane), pure fractions are combined and distilled at 14 Torr and 130°. These are obtained 5.6 g (83.5%) of (S)-cis-1-iodo-3,7-dimethyl-4-octene as a colourless liquid. $[\alpha]_D^{20} = +14.3°$ (2.21% in CHCl$_3$).

A solution of 6.1 g of (S)-cis-1-iodo-3,7-dimethyl-4-octene and 7.2 g of triphenylphosphine in 40 ml of toluene is held under reflux for 24 hours, then concentrated under reduced pressure. The residue is digested with absolute ether until only traces of triphenylphosphine are observable in the thin-layer chromatogram. There are obtained 11.8 g (97.4%) of (S)-cis-3,7-dimethyl-4-octene-1-triphenylphosphonium iodide. This is covered with 20 ml of dry ether and treated dropwise in an argon atmosphere with stirring and slight cooling to room temperature with 22.2 ml of a 2-M solution of n-butyllithium in n-hexane. The mixture is stirred for 20 seconds at room temperature, cooled down to −10° and a solution of 2.8 g of (S)-4-chloro-2-methylbutyraldehyde in 3 ml of dry ether is added dropwise thereto. The mixture is stirred for 1 hour without cooling, concentrated under reduced pressure to a small volume, the residue treated with 80 ml of dimethylformamide while cooling to room temperature and the solution subsequently stirred at room temperature for 20 hours. The reaction mixture is poured on to ice, extracted with ether, freed from traces of dimethylformamide by washing with water, dried and concentrated under reduced pressure. The residue is purified by adsorption on silicagel (elution agent: n-hexane) and distilled at 0.2 Torr and 100°. There is obtained (3S,7S)-1-chloro-3,7,11-trimethyl-4-cis/trans-8-cis-dodecadiene in a yield of 1.7 g (30.1%). $[\alpha]_D^{20} = -5.2°$ (2.11% in chloroform).

2.0 g of (3S,7S)-1-chloro-3,7,11-trimethyl-4-cis/trans-8-cis-dodecadiene are heated under reflux conditions for 24 hours with 2.5 g of triphenylphosphine in 20 ml of dry dimethylformamide. The solvent is pulled off under reduced pressure and the residue digested with dry ether until only traces of triphenylphosphine are observable in the thin-layer chromatogram. The residue, dried in the high vacuum, weighs 1.85 g (44.5% yield) and (sic) consists of (3S,7S)-3,7,11-trimethyl-4-cis/- trans-8-cis-dodecadiene-1-triphenylphosphonium chloride. There are now added under argon 10 ml of dry ether followed by 1.8 ml of 2-M n-butyllithium in n-hexane. A brown-red suspension has resulted after 5 hours. At −10° there is added dropwise in 15 minutes a solution of 900 mg of (S)-6-acetoxy-2-formyl-2,5,7,8-tetramethylchromane in 5 ml of dry ether, [the mixture] is stirred for 1 hour without cooling and then treated with 30 ml of dry dimethylformamide. The mixture is stirred further at room temperature for 18 hours, hydrolysed with ice, extracted with ether after saturation with common salt, washed free from dimethylformamide, dried and concentrated under reduced pressure. Purification is carried out by adsorption on silicagel, concentration and re-acetylation of the residue in 2 ml of dry pyridine with 2 ml of acetic anhydride (17 hours at room temperature). [The mixture] is hydrolysed with 3-N hydrochloric acid, water and aqueous sodium bicarbonate solution. After drying and concentration under reduced pressure, the residue is purified by adsorption on silicagel (elution agent: chloroform), concentrated under reduced pressure and dried up to constant weight under strongly reduced pressure. There are obtained 1.29 g (75%) of (2S)-2,5,7,8-tetramethyl-2-[(4S,8S)-4,8,12-trimethyl-1-cis/trans-5-cis/trans-9-cis-tridecatrienyl]-6-chromanyl acetate as a pale yellow, viscous oil; $[\alpha]_D^{20} = -60.7°$ (2.11% in CHCl$_3$).

The product is a mixture of cis/trans-isomers varying in composition and rotation value from batch to batch.

A solution of 321 mg of (2S)-2,5,7,8-tetramethyl-2-[(4S,7S)-4,8,12-trimethyl-1-cis/trans-5-cis/trans-9-cis-tridecatrienyl]-6-chromanyl acetate in 5 ml of pure acetic ester is hydrogenated on 35 mg of pre-hydrogenated platinum dioxide. 60.0 ml of hydrogen are taken up after 25 minutes. The mixture is filtered from catalyst, concentrated under reduced pressure and the residue is then dried under strongly reduced pressure. There are obtained 319 mg (98.1%) of (2R,4′R,8′R)-α-tocopheryl acetate as a colourless, viscous oil, $[\alpha]_D^{20} = +2.2°$ (2.09% in cyclohexane), identical with authentic material.

(2R,4′R,8′R)-α-tocopheryl acetate can also be produced starting from (3S,7S)-1-chloro-3,7,11-trimethyl-4-cis/trans-8-cis-dodecadiene in the following manner:

A solution of 1.6 g (3S,7S)-1-chloro-3,7,11-dimethyl-4-cis/trans-8-cis-dodecadiene in 20 ml of isobutyl methyl ketone is stirred at 130° (bath temperature) for 48 hours with 3.0 g of sodium iodide. The reaction mixture is cooled to room temperature, taken up in ether, washed with water and evaporated under reduced pressure. The residue is purified by adsorption on silica gel (elution agent: n-hexane). After distillation at 0.07 Torr and 100°, there are obtained 1.98 g (90%) of (3S,7S)-1-iodo-3,7,11-trimethyl-4-cis/trans-8-cis-dodecadiene as a colourless product; $[\alpha]_D^{20} = -7.3°$ (4.11% in chloroform).

The cis/trans ratio and the double bond at C-4 varies from batch to batch, and accordingly also the rotation value.

The optical purity of the product obtained is proved as follows:

It is hydrogenated on pre-hydrogenated platinum oxide, the iodine atom exchanged for the hydroxy group by heating with potassium acetate in dimethylformamide and saponification with 4-N aqueous caustic soda. The resulting product, (3R,7R)-3,7,11-trimethyl-1-dodecanol, has a rotation of $[\alpha]_D^{20} = +4°$ (4.14% in n-octane) and is accordingly identical with authentic, optically pure material.

A solution of 1.1g of (3S,7S)-1-iodo-3,7,11-trimethyl-4-cis/trans-8-cis-dodecadiene, 1.0 g of triphenylphosphine and 10 ml of xylene is heated under reflux conditions for 24 hours, then concentrated under reduced pressure. The residue is treated with dry ether until only traces of triphenylphosphine are observable in the thin-layer chromatogram. The dried residue consists of (3S,7S)-3,7,11-trimethyl-4-cis/trans-8-cis-dodecadiene-1-triphenylphosphonium iodide and weighs 1.9 g (97%).

The phosphonium salt is covered with 10 ml of dry ether and treated dropwise with 1.6 ml of 2-M n-butyllithium in n-hexane, whereupon the mixture is then stirred at room temperature for a further 2 hours. A solution of 880 ml of (S)-6-acetoxy-2-formyl-2,5,7,8-tetramethyl-chromane in 10 ml of dry ether is added dropwise at −15° in 15 minutes, the mixture is then stirred for 1 hour without cooling and then treated with 30 ml of dry dimethylformamide. The mixture is stirred at room temperature for 20 hours, hydrolysed with ice, extracted with ether after saturation with common salt. The extract washed with water, dried and concentrated under reduced pressure. Purification is carried out by adsorption on silicagel (elution agent: chloroform), concentrating and re-acetylating the residue in 2 ml of dry pyridine with 2 ml of acetic anhydride (17 hours at room temperature). The mixture is hydrolysed with ice, extracted with ether and the ether phase washed with 3-N hydrochloric acid, water and aqueous sodium bicarbonate solution. After drying and concentration under reduced pressure, the residue is again purified by adsorption on silicagel (elution agent: chloroform), concentration under reduced pressure and then dried up to constant weight under strongly reduced pressure. There are obtained 459 mg (31%) of (2S)-2,5,7,8-tetramethyl-2-[(4S,8S)-4,8,12-trimethyl-1-cis/trans-5-cis/trans-9-cis-tridecatrienyl]-6-chromanyl acetate as a pale yellowish oil. $[\alpha]_D^{20} = -41.3°$ (0.75% in CHCl$_3$).

The product is a mixture with varying composition of cis/trans-isomers which also have differing rotation values.

A solution of 400 mg of (2S)-2,5,7,8-tetramethyl-2-[(4S,8S)-4,8,12-trimethyl-1-cis/trans-5-cis/trans-9-cis-tridecatrienyl]-6-chromanyl acetate in 5 ml of pure acetic ester is hydrogenated on 500 mg of pre-hydrogenated platinum dioxide. 68 ml of hydrogen are taken up after 40 minutes. [The mixture] is filtered off from catalyst, concentrated under reduced pressure and then dried under strongly reduced pressure. There are obtained 396 mg (97.7%) of (2R,4′R,8′R)-α-tocopheryl acetate in 99.7% purity. $[\alpha]_D^{20} = +2.2° \pm 0.5°$ (1.07% in cyclohexane), identical with authentic (2R,4′R,8′R)-α-tocopheryl acetate.

EXAMPLE 13

To 2.3 ml of a solution of 1.01-N sodium ethylate in ethanol in a flask provided with reflux condenser and calcium chloride tube are added dropwise 300 mg (2.3 mmol) of acetic acid ethyl ester and subsequently 671 mg (2.3 mmol) of (3R,7R)-1-bromo-3,7,11-trimethyldodecane in 2 ml of ethanol. This mixture is boiled under reflux for 15 hours while stirring. After cooling, so much ice water is added that the separated salt is just dissolved, the organic phase is separated in a separating funnel and shaken out four times with methylene chloride. After drying the combined organic phases over magnesium sulphate and distillation of the solvent, there are obtained 755 mg of crude (5R,9R)-2-acetyl-5,9,13-trimethyltetradecanoic acid ethyl ester. For analytical purposes a sample of the crude (5R,9R)-2-acetyl-5,9,13-trimethyl-tetradecanoic acid ethyl ester is chromatographed on a preparative silicagel plate with toluene/hexane/acetic acid ethyl ester = 30:10:3 and the thus obtained pure (5R,9R)-2-acetyl-5,9,13-trimethyl-tetradecanoic acid ethyl ester is distilled at 150°/0.03 Torr; $[\alpha]_{365}^{20} = -4.0°$ (c = 1.04; CHCl$_3$).

A solution of 154 mg of (5R,9R)-2-acetyl-5,9,13-trimethyltetradecanoic acid ethyl ester in 5 ml of ethanol is treated dropwise at a temperature of 80° with 1 ml of 10% caustic soda. The reaction mixture is subsequently boiled under reflux for 3.5 hours. The cold reaction mixture is neutralised with 1-N aqueous hydrochloric acid and extracted four times with methylene chloride. The combined organic phases are washed first with saturated common salt solution and then dried over magnesium sulphate. After removal of the solvent under reduced pressure and distillation at 150°/0.03 Torr there are obtained 118 mg (95%) of (6R,10R)-14-trimethylpentadecanone-2 (hexahydrofarnesylacetone). $[\alpha]_{330}^{20} = +7.55°$ (c = 1.57; n-octane). The ORD spectrum is identical with that of (6R,10R)-14-trimethylpentadecanone-2 prepared from natural phytol (Helv. Chem. Acta, 47, 1964, pages 221 et seq).

The (6R,10R)-14-trimethylpentadecanone-2 obtained can be converted into natural vitamin K$_1$, e.g., in accordance with J. Chem. Soc. (C), 1966, pages 2144–2176 or Helv. Chim. Acta, 48, 1965, pages 1332–1347.

We claim:

1. A process for producing a tertiary optically active aliphatic compound of the formula

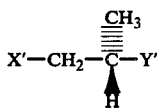   II wherein X' and Y' are different functional groups, one is carboxy, esterified carboxy and the other is carboxy, hydroxymethyl, esterified carboxy or etherified or esterified hydroxymethyl; wherein the carboxy and hydroxymethyl groups are lactonized with one another with the formation of the group —CO—O—CH$_2$— or —CH$_2$—O—CO—, and wherein when X' is alkyl-etherified hydroxymethyl, Y' is also hydroxymethyl or esterified hydroxymethyl, comprising fermentatively hydrogenating an olefinic compound of the formula:

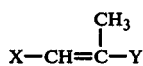   I wherein X is carboxy, esterified carboxy, hydroxymethyl etherified or esterified hydroxymethyl and Y is carboxy, formyl, hydroxymethyl, esterified carboxy, acetalized formyl or etherified or esterified hydroxymethyl; wherein X and Y are different functional groups; wherein when X is hydroxymethyl or esterified hydroxymethyl, Y is carboxy, formyl, or acetalized formyl and when Y is hydroxymethyl or esterified hydroxymethyl, X is esterified carboxy or alkyl-etherified hydroxymethyl, with an aerobic or facultative microorganism capable of hydrogenating a double bond situated in an aliphatic chain between a CH and methylated CH moiety in an aqueous medium to obtain said tertiary optically active aliphatic compound as a fermentation product.

2. The process of claim 1 wherein one of X and Y is esterified carboxy or acetalized formyl.

3. The process of claim 2 wherein one of X and Y is

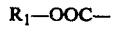

wherein R$_1$ is lower alkyl, phenyl or phenyl lower alkyl.

4. The process of claim 1 wherein one of X and Y is hydroxymethyl or esterified or etherified hydroxymethyl.

5. The process of claim 4 wherein one of X and Y is

wherein R$_2$ is lower alkyl or acyl.

6. The process of claim 1 wherein one of X and Y is

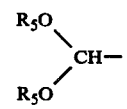

wherein R$_5$ is individually lower alkyl or taken together forms lower alkylene.

7. The process of claim 1 wherein the fermentative hydrogenation is carried out under aerobic conditions with a microorganism in the stationary phase.

8. The process of claim 7 wherein the fermentation hydrogenation is carried out in the presence of an assimilable carbon source.

9. The process of claim 8 wherein the carbon source is sugar present in an amount of from about 10 to about 100 g per liter of aqueous medium.

10. The process of claim 1 wherein the fermentative hydrogenation is carried out at a pH of from about 2 to 10 and a temperature of from about 20° to 35° C.

11. The process of claim 10 wherein the olefinic compound is present in a concentration of 0.1–5.0% based on the aqueous medium.

12. The process of claim 1 wherein X is carboxy or esterified carboxy and Y is formyl or acetalized formyl or X is esterified carboxy and Y is hydroxymethyl, etherified or esterified hydroxymethyl, and the microorganism is Saccharomyces cerevisiae, to obtain a fermentation product where X' is carboxy or esterified carboxy and Y' is hydroxymethyl or etherified or esterified hydroxymethyl wherein the carboxy and hydroxymethyl groups are lactonized with one another with the formation of the group —CO—O—CH$_2$—.

13. The process according to claim 12 wherein X is carboxy or esterified carboxy and Y is formyl or acetalized formyl.

14. The process according to claim 13 wherein the olefinic compound is ethyl-trans-4,4-dimethoxy-3-methylcrotonate.

15. The process of claim 1 wherein one of X and Y is carboxy and the other represents esterified carboxy, and the microorganism is Saccharomyces cerevisiae to obtain a fermentation product where one of the X' and Y' is carboxy and the other is esterified carboxy.

16. The process of claim 15 wherein X is esterified carboxy and Y is carboxy.

17. The process of claim 1 wherein X is esterified carboxy and Y is formyl or acetalized formyl or hydroxymethyl or esterified hydroxymethyl, and the microorganism is Geotrichum candidum, to obtain a fermentation product where X' represents esterified carboxy and Y' represents carboxy.

18. The process of claim 1 wherein X is hydroxymethyl or esterified hydroxymethyl and Y is formyl, acetalized formyl or esterified carboxy, and the microorganism is Geotrichum candidum, to obtain a fermentation product where X' is hydroxymethyl or esterified hydroxymethyl and Y' is carboxy or esterified carboxy with the free carboxy and hydroxymethyl groups being lactonized with one another to form the group —CH$_2$—O—CO.

19. The process of claim 18 wherein X is hydroxymethyl or esterified hydroxymethyl and Y is formyl or acetalized formyl.

20. Process according to claim 19 where the olefinic compound is trans-3-(1,3-dioxolan-2-yl)-2-buten-1-ol and the fermentation product is (S)-dihydro-3-methyl-2(3H)-furanone.

21. The process of claim 1 wherein X is alkyl-etherified hydroxymethyl and Y is formyl, acetalized formyl, hydroxymethyl or esterified hydroxymethyl, the microorganism is Saccharomyces cerevisiae to obtain a fermentation product wherein X' is alkyl-etherified hydroxymethyl and Y' is hydroxymethyl or esterified hydroxymethyl.

22. The process of claim 21 wherein the olefinic compound is trans-1,1,4-trimethoxy-2-methyl-2-butene, trans-4-methoxy-2-methyl-2-buten-1-ol or trans-4-methoxy-2-methyl-2-buten-1-ol-acetate and the fermentation product is (S)-4-methoxy-2-methylbutan-1-ol.

23. The process of claim 1 wherein X is alkyl-etherified hydroxymethyl and Y is formyl, acetalized formyl, hydroxymethyl or esterified hydroxymethyl and the microorganism is Geotrichum candidum to obtain a fermentation product of where X' is alkyletherified hydroxymethyl and Y' is carboxy.

24. The process of claim 1 wherein the olefinic compound is trans-1,1,4-trimethoxy-2-methyl-2-butene, trans-4-methoxy-2-methyl-2-buten-1-ol, trans-4-methoxy-2-methyl-2-buten-1-ol-acetate, trans-4-methoxy-2-methyl-crotonaldehyde or trans-2-(3-methoxy-1-methylpropenyl)-1,3-dioxolan and the fermentation product is (S)-4-methoxy-2-methyl-butyric acid.

* * * * *